US009045714B2

(12) United States Patent
Oertling et al.

(10) Patent No.: US 9,045,714 B2
(45) Date of Patent: Jun. 2, 2015

(54) DIHYDROBENZOFURAN DERIVATIVES AS FRAGRANCE AND/OR FLAVORING MATERIALS

(71) Applicant: Symrise AG, Holzminden (DE)

(72) Inventors: Heiko Oertling, Lausanne (CH); Claudia Gömann, Golmbach-Warbsen (DE); Marc Vom Ende, Bodenwerder (DE)

(73) Assignee: Symrise AG, Holzminden (DE)

( * ) Notice: Subject to any disclaimer, the term of this patent is extended or adjusted under 35 U.S.C. 154(b) by 111 days.

(21) Appl. No.: 13/838,855

(22) Filed: Mar. 15, 2013

(65) Prior Publication Data

US 2013/0243716 A1 Sep. 19, 2013

(30) Foreign Application Priority Data

Mar. 19, 2012 (EP) .................................... 12160062

(51) Int. Cl.

*C11B 9/00* (2006.01)
*A23L 1/226* (2006.01)
*C07D 307/80* (2006.01)

(52) U.S. Cl.

CPC ........... *C11B 9/0076* (2013.01); *A23L 1/22671* (2013.01); *C07D 307/80* (2013.01)

(58) Field of Classification Search

CPC C07D 307/80; A23L 1/22671; C11B 9/0076; A61Q 13/00
USPC ............................................................ 512/1
See application file for complete search history.

(56) References Cited

U.S. PATENT DOCUMENTS 3,551,456 A * 12/1970 Bloch .......................... 549/405

FOREIGN PATENT DOCUMENTS

WO 2007030061 A1 3/2007
WO WO 2007030061 A1 * 3/2007

OTHER PUBLICATIONS

Kraft Philip Ed—David J Rowe: "Aroma Chemicals IV: Musks", Mar. 3, 2009, Chemistry and Technology of Flavors and Fragrances, Blackwell Publishing Ltd, pp. 143-168, XP009159883, ISBN: 978-1-4443-0551-7.

Shi, G., Cottens,S,, Shiba, S., Schlosser,M.: "The Diels-Alder Approach to Musk Odor type Arenes", Tetrahedron, Bd. 48, Nr. 48, 1992, Seiten 10569-10574.

Dadush et al: "Microwave activation of aluminia and its use as a catalyst in syntheiic reactions", Journal of Chemical Research, Science Reviews 2000 Ltd, Jan. 1, 2009, Seiten 120-123, XP009159883.

European Search Report dated Jun. 12, 2012 for priority application EP12160062.1-2117.

* cited by examiner

*Primary Examiner* — Ling Choi
*Assistant Examiner* — Lanee Reuther
(74) *Attorney, Agent, or Firm* — Dilworth & Barrese, LLP

(57) ABSTRACT

Compounds and methods of using of compounds or mixtures thereof, as fragrance and/or flavoring material or as fragrance and/or flavoring material mixture, new fragrance and/or flavoring material mixtures, new perfumed and/or flavored articles, and new, particularly advantageous compounds and mixtures to be used are described.

20 Claims, No Drawings

DIHYDROBENZOFURAN DERIVATIVES AS FRAGRANCE AND/OR FLAVORING MATERIALS

CROSS-REFERENCE TO RELATED APPLICATIONS

This application claims the benefit of European Patent Application 12 160 062.1, filed on 19 Mar. 2012, entitled Dihydrobenzofuran Derivates As Fragrance And/Or Flavoring Materials which is incorporated herein by reference in its entirety as if fully set forth below.

TECHNICAL FIELD

The various embodiments of the disclosure relate generally to fragrance and/or flavoring compositions, their use and manufacture, and articles containing the compositions, and more particularly to dihydrobenzofurans as a flavor or fragrance component.

BACKGROUND OF THE INVENTION

Although numerous fragrance and flavoring materials already exist, in the perfume industry there is still a general demand for new fragrance and flavoring materials. Thus, there is in particular a need for fragrances with musk perfume notes, in particular fragrances that are able to produce, in addition to a musk perfume note (in fragrance mixtures), additional interesting odor notes, and are able, with their novel or original fragrance properties, to expand the perfumer's capabilities. In particular there is interest in fragrances with musk perfume notes that can be combined harmoniously with fragrance materials with a woody and/or floral fragrance and/or other musk fragrances. Preferably various olfactory aspects and fragrance notes should be superimposed, so as to produce an overall complex odor impression.

For creating novel modern compositions, there is a constant need for fragrances with particular (olfactory) properties, which are suitable for serving as a basis for the compositions of novel modern perfumes with a complex odor character. Preferred fragrances should have, in addition to a musk perfume note, other notes and/or aspects or properties, which endow them with a particularly olfactory character and complexity and ideally further positive properties.

The object to be achieved by the present invention was basically to provide fragrance and/or flavoring materials with musk (fragrance) notes, which preferably have further interesting and original (olfactory) properties, so that novel and original fragrance and/or flavoring material mixtures with special (olfactory) notes and aspects can be produced. In particular it was a matter of providing fragrances with musk perfume notes, which are in particular suitable for combining with further fragrances, e.g. for combining with further fragrances that possess a floral perfume note The preferred object of the present invention was to provide flavoring and/or fragrance materials that possess, in addition to their advantageous primary, in particular olfactory, properties, additionally advantageous secondary properties, e.g. greater stability under certain conditions of use, higher yield, better adhesiveness, high substantivity, an advantageous booster effect and/or a strong blooming, so that sensorially advantageous effects and/or better dermatological and toxicological properties can be achieved, versus comparable fragrance or flavoring materials.

A particularly preferred task of the present invention was to provide flavoring or fragrance materials that have, in addition to their sensory properties, improved biodegradability and reduced bioaccumulation. In particular, the class of polycyclic musks (PCMs), to which commercially successful representatives of the synthetic musks belong, has the drawback of inadequate biodegradability. As a consequence of this inadequate degradability, such substances accumulate in the environment and, among other things via the food chain, become enriched or accumulate in various organisms (bioaccumulation). Owing to the lipophilic character of these substances, they can be detected in the fat tissue of mammals (see for example: "*Poly-musk compounds in human blood II—Human biomonitoring of musk odorants*", M. Uhl (Umweltbundesamt GmbH Austria), H. P. Hutter (Institut für Umwelthygiene, Public Health, Medical University Vienna), G. Lorbeer (Analytik AII, Umweltbundesamt GmbH Austria)).

An example from the group of polycyclic musk compounds is Galaxolide® (also called HHCB, $C_{18}H_{26}O$, CAS number: 1222-05-5, source: Umweltprobenbank des Bundes [Environmental sample database of the Federation]). HHCB is at present the globally most frequently used substance from the group of polycyclic musk compounds. HHCB is a polycyclic musk compound, which is used as a synthetic odorant for example in cosmetics and body-care products such as soaps, shampoos, lotions, deodorants, in washing and cleaning agents, air fresheners, paper and textiles. After use, HHCB enters the environment, via wastewater and sewage sludge, and is degraded there very slowly. HHCB is lipophilic and accumulates in organisms (bioaccumulation).

Poor biodegradability and bioaccumulation tendency are linked directly to the properties of the materials, for example water solubility, lipophilic character and the distribution coefficient in octanol/water. These properties arise in their turn from the chemical structure of a substance.

It can generally be stated that in the carbon backbone of the common fragrances, oxygen substitution (i.e. replacement of a carbon atom with an oxygen atom) promotes better or faster biodegradability or in fact makes it possible at all. The substitution leads to higher polarity of the substance and therefore lower lipophilicity. It is to be assumed that materials with increased oxygen substitution also display less bioaccumulation.

To summarize, the primary object to be achieved by the present invention was to provide preferably biodegradable fragrance and/or flavoring materials with musk (fragrance) notes and further advantageous properties, as described above.

Another object was to provide new fragrance and/or flavoring materials, new fragrance and/or flavoring material mixtures and new perfumed and/or flavored products.

Further objects to be achieved by the present invention can be seen from the following description and in particular the appended patent claims.

BRIEF SUMMARY

The present invention relates to the use of individual compounds of formula (I)

(I)

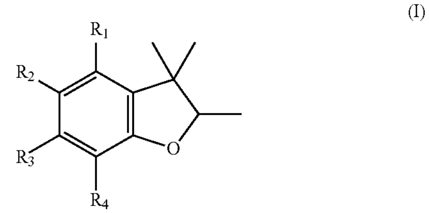

or mixtures thereof, in particular mixtures of two, three, four, five, six or a plurality of different compounds of formula (I) as fragrance and/or flavoring material or as fragrance and/or flavoring material mixture. The residues $R_1$ through $R_4$ have the meaning described in the context of the present text.

The invention also relates to novel fragrance and/or flavoring material mixtures, which in addition to a compound of formula (I) or a mixture thereof, as described in each case herein, comprise or consist of one or a plurality of, in particular two, three or a plurality of, further fragrance and/or flavoring materials that are not compounds of formula (I).

Furthermore, the present invention relates to perfumed and/or flavored articles that contain a fragrance and/or flavoring material mixture according to the present invention.

In the context of the present invention, compounds of formula (I) and mixtures thereof that are novel relative to the prior art, and particularly advantageous, are also described.

The present invention also relates to a method of imparting, modifying and/or intensifying an odor and/or taste, preferably a musky and/or woody odor and/or taste.

Further aspects of the present invention can be seen from the following description and in particular the appended patent claims

DETAILED DESCRIPTION

Although preferred embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. The disclosure is capable of other embodiments and of being practiced or carried out in various ways. Also, in describing the preferred embodiments, specific terminology will be resorted to for the sake of clarity.

It must also be noted that, as used in the specification and the appended claims, the singular forms "a," "an" and "the" include plural referents unless the context clearly dictates otherwise.

Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" one particular value and/or to "about" or "approximately" another particular value. When such a range is expressed, another embodiment includes from the one particular value and/or to the other particular value.

By "comprising" or "comprising" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

The primary object to be achieved by the present invention is achieved by using a compound of formula (I)

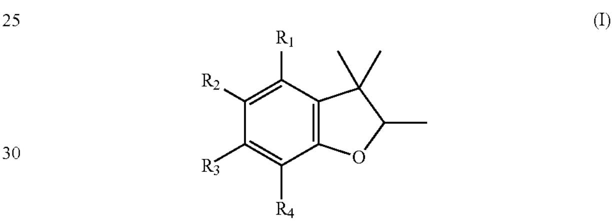

(I)

or a mixture of two, three, four, five, six or a plurality of different compounds of formula (I), wherein it applies, respectively, to the residues of the compound of formula (I) or the residues of all compounds of formula (I), that $R_1$, $R_2$, $R_3$ and $R_4$, in each case independently of one another, denote hydrogen, methyl, ethyl, propyl, isopropyl, butyl, sec-butyl, tert-butyl, isobutyl, acetyl, formyl or cyano, as fragrance and/or flavoring material or as fragrance and/or flavoring material mixture, in particular as fragrance or as fragrance mixture.

In the context of the present invention, compounds of the above formula (I) and mixtures thereof that are novel relative to the prior art have also been found. These are described below.

The compounds to be used according to the invention are advantageously able both to satisfy the perfumery requirements, and possess a particularly advantageous biodegradability.

It was particularly surprising that precisely the compounds of formula (I) described herein are suitable for the purposes of the present invention. Thus, the search for suitable fragrances, was—and usually is—hampered by the following circumstances:

The mechanisms of odor perception are (still) not adequately known.

The relationships between the special odor perception on the one hand and the chemical structure of the associated fragrance on the other hand have (still) not been investigated sufficiently.

Often even just slight changes in the structural make-up of a known fragrance bring about marked changes in sensory (or other) properties. These may, moreover, impair the compatibility with the human body.

Therefore as a rule the manner in which structural changes affect the sensory (and optionally other) properties of a substance can only be predicted to a limited extent, or not at all.

The compounds of formula (I), as described herein, are not only basically more highly oxygen-substituted than materials used commercially hitherto, but (also or in particular) are oxygen-substituted on the aromatic nucleus, which is difficult to oxidize. The degradation of aromatic hydrocarbon compounds in the environment begins as a rule with an oxidative step, which is induced by aerobic degradation by microorganisms. Through the oxygen substitution on the aromatic nucleus, a (further) microbial metabolization (to catechol), in contrast to unoxidized substances, advantageously takes place by means of a phenol mono-oxygenase instead of a dioxygenase. The aerobic degradation of phenolic aromatics therefore as a rule takes place more easily and more quickly than the aerobic degradation of unoxidized substances (cf. for example "*Microbiological transformation of selected groups of substances: aromatic hydrocarbons*" in "*Chemie and Biologie der Altlasten" [Chemistry and biology of contaminated sites*], published by the Fachgruppe Wasserchemie der GdCh [Water Chemistry Technical Group of the Society of German Chemists], VCH, Weinheim, 1997).

In particular in view of the aforementioned difficult circumstances in the search for suitable fragrances, it was surprising that the compounds of formula (I) to be used according to the invention also possess particularly advantageous sensory properties, in addition to advantageous biodegradability. Furthermore, in addition to their primary, in particular olfactory, properties, these compounds possess (further) positive secondary properties. For example, they possess or impart improved adhesiveness and high substantivity (relative to fragrances with similar odor properties). The compounds to be used according to the invention or the corresponding mixtures advantageously also possess high stability under various conditions of use and have a high yield.

The compounds of formula (I) can optionally each be in the form of pure stereoisomers or mixture of stereoisomers. In particular, a compound of formula (I) can be in the form of enantiomer or mixture of enantiomers.

The compounds of formula (I) to be used according to the invention have particularly advantageous musky notes. Accordingly, in the context of the present invention, a use of a compound of formula (I) or of a mixture of a plurality of different compounds of formula (I) described herein is particularly preferred, wherein the compound or the mixture is used as fragrance and/or flavoring material with musky note or as fragrance and/or flavoring material mixture with musky note.

A use according to the invention of a compound of formula (I) or of a mixture of a plurality of different compounds of formula (I) described herein for imparting, modifying and/or intensifying an odor and/or a taste, preferably a musky odor, in particular a radiant musky odor, an exalting odor and/or a woody, in particular a softly woody odor, is particularly preferred.

Basically, the sensory properties, in particular the odor properties, of compounds of formula (I) to be used according to the invention can be described in particular as follows: strongly radiant, musky, exalting, soft, reminiscent of ambrette seed oil, very natural (odor) impression. The compounds of formula (I) to be used according to the invention or corresponding mixtures can be used advantageously in particular for imparting, modifying and/or intensifying a corresponding odor and/or taste note.

In view of the prior art, the area of fragrance chemistry described herein can be considered to be well-researched (e.g. in connection with the products Traseolide®, Celestolide® and Phantolide®). Therefore it was particularly surprising that new, particularly valuable fragrances could now be found or identified as suitable according to the invention. Furthermore, the compounds of formula (I) to be used according to the invention, in particular the compounds of formula (I) described herein that are novel relative to the prior art, possess independent olfactory properties versus existing fragrances, which are clearly different from the known fragrances and are partly even superior to the latter.

The odor descriptions of Traseolide®, Celestolide® and Phantolide® can be summarized as follows:

Celestolide®: strong musk note
Traseolide®: woody, musky
Phantolide®: musky

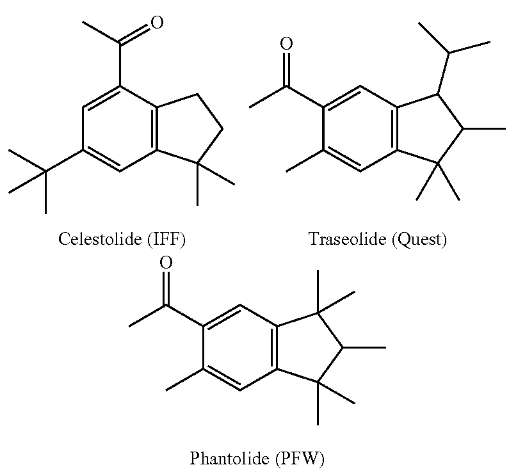

The methylation pattern on the five-membered ring (see above) is characteristic of the compounds of formula (I) to be used according to the invention. Furthermore, one carbon atom of the five-membered ring, as described above, is (oxygen-) substituted.

Structurally similar compounds are described in WO 96/03396. However, in contrast to the compounds of formula (I) to be used according to the invention, the compounds described therein lack a methyl group in the 2-position, as can be seen from the following example:

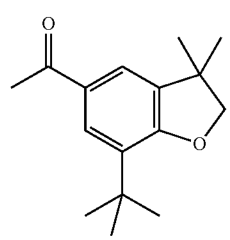 [SMILES: CC(=O)c1cc(C(C)(C)C)c2c(c1)C(C)(C)CO2]

In addition, no sensory properties of these compounds are described in WO 96/03396. Rather, the anti-inflammatory properties of the substances described therein are stressed.

This also applies to the following compound, which is mentioned in WO 97/28148 as an intermediate in a synthesis sequence:

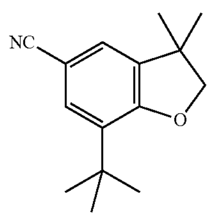 [SMILES: CC(C)(C)c1cc(C#N)cc2c1OCC2(C)C]

In WO2007/030061, the following compounds are described as synthesis intermediates in a 1:1 mixture:

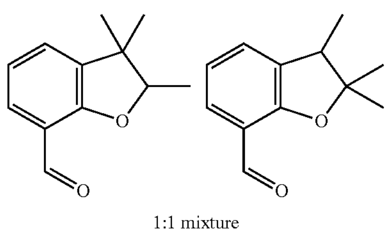

1:1 mixture

The sensory properties of the compounds to be used according to the invention have not been recognized or suggested in the prior art.

The suitability of coumaran and chroman derivatives for use as fragrance and/or flavoring materials is described in U.S. Pat. No. 3,551,456. For example, the condensation of phenol, monoalkylated phenols and symmetrically substituted bisalkylphenols (e.g. 2,4-dipropylphenol) under acidic conditions (e.g. with phosphoric acid, sulfuric acid or a Lewis acid) with a conjugated diene (e.g. butadiene, pentadiene or hexadiene), is described.

The condensation takes place naturally non-regioselectively, and mixtures of the polyalkylated coumarans and chromans are obtained. According to U.S. Pat. No. 3,551,456, these are separated by means not employing distillation. Then according to U.S. Pat. No. 3,551,456 the mixtures obtained are acetylated under Friedel-Crafts conditions.

The mixtures obtained are described in olfactory terms as having a musk character. The following isomers are listed in U.S. Pat. No. 3,551,456 as individual substances with an acetylated coumaran structure:

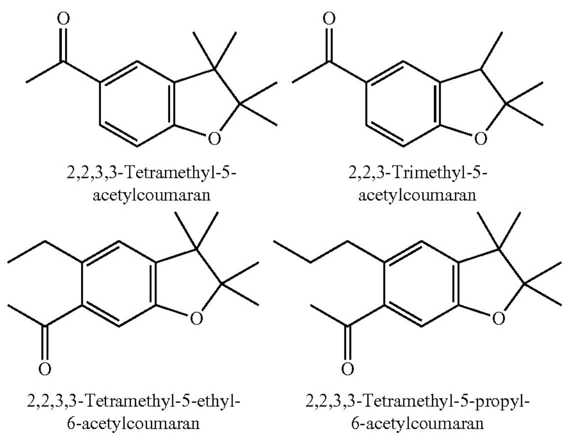

2,2,3,3-Tetramethyl-5-acetylcoumaran 2,2,3-Trimethyl-5-acetylcoumaran 2,2,3,3-Tetramethyl-5-ethyl-6-acetylcoumaran 2,2,3,3-Tetramethyl-5-propyl-6-acetylcoumaran -continued

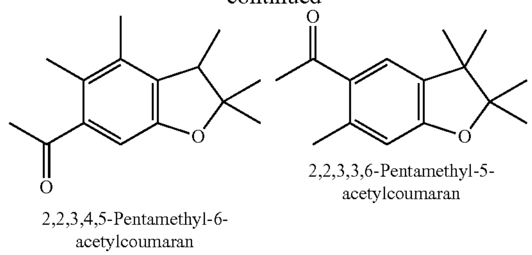

2,2,3,4,5-Pentamethyl-6-acetylcoumaran 2,2,3,3,6-Pentamethyl-5-acetylcoumaran

However, none of the compounds concretely described in U.S. Pat. No. 3,551,456 has the characteristic 2,3,3-trimethyl-(coumaran) substitution pattern for the compounds of formula (I) to be used according to the invention.

Furthermore, in general, no compounds of formula (I) can be obtained under the reaction conditions described in U.S. Pat. No. 3,551,456.

According to "Example II" of U.S. Pat. No. 3,551,456, mixtures of trimethylcoumarans, which are not specified in more detail, are indeed obtained by direct acid condensation of phenol with isoprene by phosphoric acid. However, after acetylation under Friedel-Crafts conditions and then distillation, 2,2,3-trimethylacetylcoumarans are obtained that do not correspond to formula (I).

The acid condensation of phenol with isoprene and phosphoric acid is a reaction that has been investigated thoroughly in the chemical literature. As examples, reference may be made in this connection to the following sources:

L. Claisen, Chemische Berichte 1921, 54, 200 ff: 2,2-dimethylchroman derivatives are described Bader et al., Journal of the American Chemical Society 1958, 80, 3073 ff:

the reaction with 71% phosphoric acid in toluene at 20° C. for 16 hours, chroman derivatives and ortho- and para-phenol derivatives are described GB 906483, Bayer, 1962:

the reaction of phenol with isoprene under aluminum phenoxide catalysis is described, wherein the following isomers are obtained:

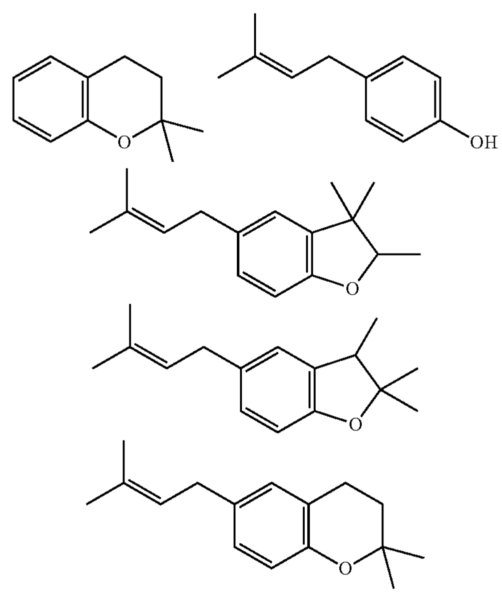

Furthermore, the reaction of para-cresol with isoprene under aluminum phenoxide catalysis is described, wherein the following isomers are obtained:

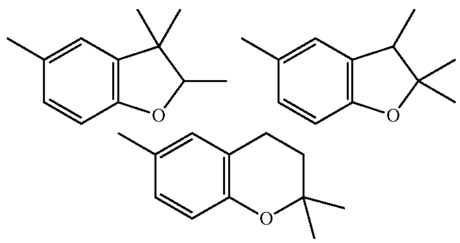

K. C. Dewhirst, F. F. Rust, Journal of Organic Chemistry 1963, 28, 798 ff.:

the reaction of phenol with isoprene under aluminum phenoxide catalysis, wherein no coumaran derivatives are formed, is described E. A. Vdovtsova, Zhurnal Organicheskoi Khimii 1965, Vol. 1, 2192 ff.:

the reaction with 71% and 100% phosphoric acid without solvent is described; no coumaran derivatives are described In U.S. Pat. No. 4,107,324, Bayer, 1978, it is mentioned that indane derivatives can be obtained by condensation of phenol and isoprene with phosphoric acid.

D. M. X. Donnelly et al., Journal of Chemical Research, Synopses (1980), (1), 1, 127 ff.:

a reaction with 71% phosphoric acid, in which an ortho-prenylated derivative is obtained, is described J. P. Ward et al., Chemistry & Industry 1989, 345 ff.:

the reaction of phenol and isoprene with aluminum phenolate is described, wherein chroman and para-phenol derivative are obtained

WO 2007/000582:

phenol, phosphorus pentoxide and phosphoric acid in meta-xylene are described, from which indenol is produced King Kuok (Mimi) Hii et al. Chem. Commun. 2008, 2325 ff.:

a reaction with copper triflate to chroman derivative is described

Hintermann et al. Journal of Organic Chemistry 2011, 76, 9353 ff.:

the reaction of phenol with isoprene and various Lewis acids (triflate salts) to chromanene is described It was particularly surprising that the compounds of formula (I) possess very useful sensory (and other positive) properties, as described herein, and basically display a strong effect in perfume formulations.

Compounds and mixtures that are particularly preferred according to the invention and are particularly suitable for the purposes of the present invention are described in the following.

A use (as described above) is preferred according to the invention, wherein for the compound of formula (I) or one, a plurality of or all compounds of formula (I), in each case independently of one another, the following applies:

$R_1$ denotes hydrogen, methyl, acetyl or formyl, preferably hydrogen or methyl, and/or $R_2$ denotes methyl, formyl or acetyl, preferably formyl or acetyl, and/or $R_3$ denotes hydrogen or methyl, and/or $R_4$ denotes methyl, ethyl, propyl, isopropyl, butyl, sec-butyl, tert-butyl or isobutyl, preferably methyl, ethyl, isopropyl or tert-butyl.

A use is particularly preferred wherein for the compound of formula (I) or one, a plurality of or all compounds of formula (I), in each case independently of one another, the following applies:

$R_1$ denotes hydrogen, methyl, acetyl or formyl, preferably hydrogen or methyl, $R_2$ denotes methyl, formyl or acetyl, preferably formyl or acetyl, $R_3$ denotes hydrogen or methyl and $R_4$ denotes methyl, ethyl, propyl, isopropyl, butyl, sec-butyl, tert-butyl or isobutyl, preferably methyl, ethyl, isopropyl or tert-butyl.

The following compounds 1 through 8 are particularly suitable for the purposes of the present invention:

COMPOUND 1

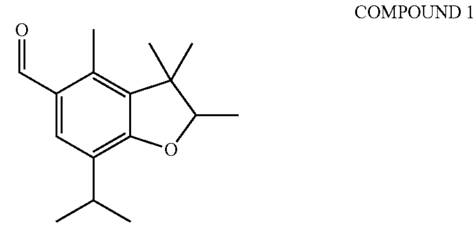

COMPOUND 2

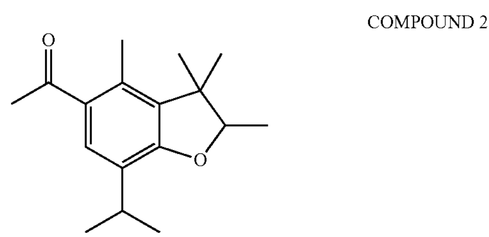

COMPOUND 3

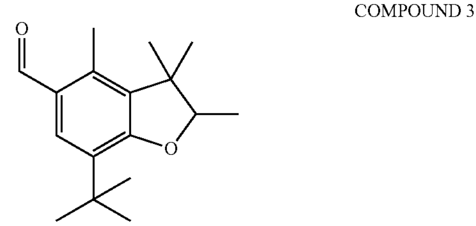

COMPOUND 4

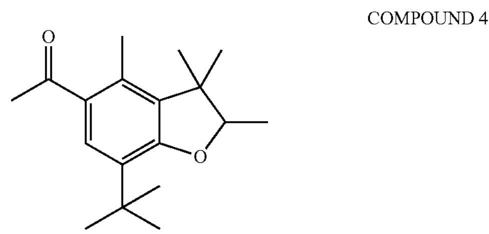

COMPOUND 5

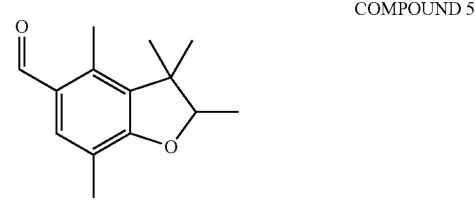

-continued

COMPOUND 6

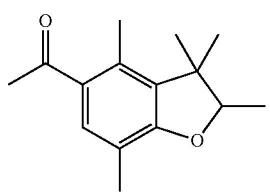

COMPOUND 7

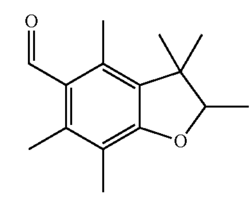

COMPOUND 8

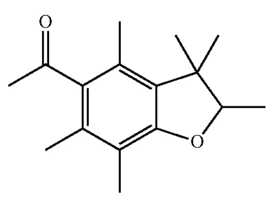

Accordingly, a use (as described above) is particularly preferred wherein the compound of formula (I) or one, a plurality of or all compounds of formula (I) is selected, or in each case independently of one another are selected, from the group consisting of the compounds 1 through 8, in particular from the compounds 2, 4 and 5.

The compounds of formula (I) to be used according to the invention can be produced by reactions and methods that are known per se (cf. the appended examples). For example, first the corresponding phenols and cresols can be reacted with allyl chloride or allyl bromide under basic conditions in good yields to the corresponding prenyl ethers.

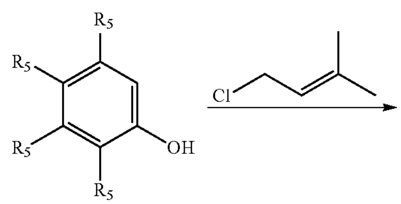

-continued $R_5$ = H or alkyl ($C_1$-$C_4$)

Then the corresponding prenyl ethers can be converted for example at 210° C. and with a catalytic amount of base to the compounds of formula (I) to be used according to the invention.

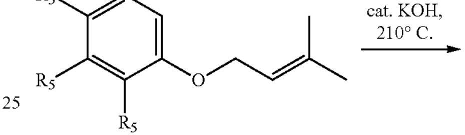

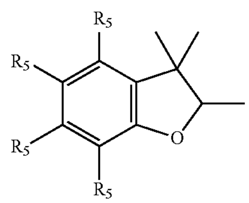

$R_5$ = H or alkyl ($C_1$-$C_4$)

A similar reaction has already been described in Kabalka et al., Journal of Chemical Research 2009, 120-123. There, the rearrangement and subsequent cyclization of prenylphenyl ethers in the presence of aluminum oxide and using microwaves to 2,3,3-trimethyldihydrobenzofurans is described. Then the trimethyldihydrobenzofurans are acetylated or formylated under standard conditions.

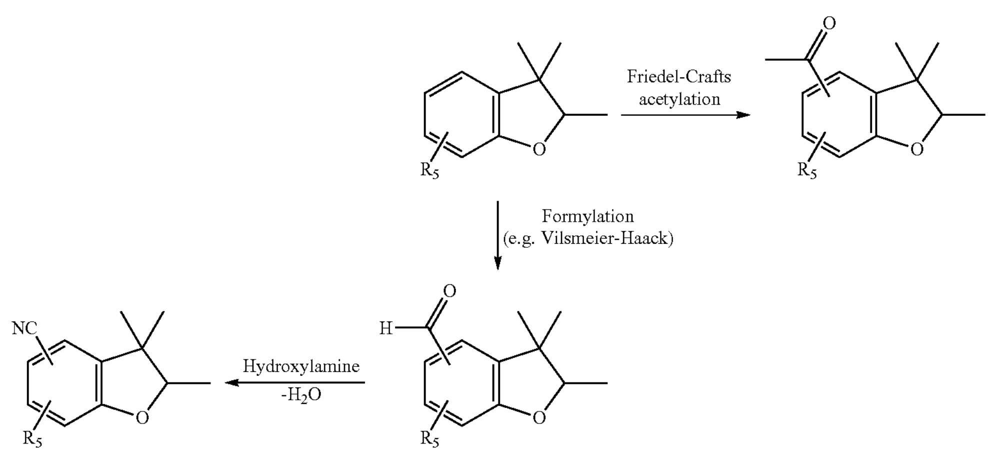

$R_5$ = H or alkyl ($C_1$-$C_4$)

The formylated compounds can be converted, in the context of the present invention, to nitriles that are preferred according to the invention.

For further practical examples for the production of compounds of formula (I) to be used according to the invention, reference may be made to the appended examples.

Another aspect of the present invention relates to fragrance and/or flavoring material mixtures according to the invention.

Accordingly, in the context of the present invention, a fragrance and/or flavoring material mixture, preferably a fragrance mixture, is also provided, comprising or consisting of (a) a compound of formula (I) or a mixture of two, three, four, five, six or a plurality of different compounds of formula (I), in each case as defined above, preferably as designated above as preferred, and (b) one, two, three or a plurality of further fragrance and/or flavoring materials, wherein the further fragrance or flavoring materials are not compounds of formula (I).

For the compounds of formula (I) contained therein or corresponding mixtures thereof, the foregoing applies in each case correspondingly. Accordingly, a fragrance and/or flavoring material mixture according to the invention preferably contains those compounds of formula (I) or mixtures thereof that are designated herein as preferred.

The compound(s) of formula (I) is/are usually contained in sensorially effective amounts.

A fragrance and/or flavoring material mixture (as described above) is particularly preferred according to the invention, wherein the or one, two, three, a plurality of or all of the further fragrance or flavoring materials according to ingredient (b) impart a woody, a musky and/or a floral odor and/or taste.

According to a preferred aspect of the present invention, the or one is or two, three, a plurality of or all of the further fragrance or flavoring materials according to ingredient (b) are fragrances with woody odor or with woody note (incl. sandalwood and ambergris) or fragrances with floral odor or floral note.

Particularly suitable woody fragrances are: sandranol (2-ethyl-4-(2,2,3)-trimethylcyclopent-3-yl-but-2-en-1-ol), Ysamber K (1',1',5',5'-tetramethylhexahydro-spiro[1,3-dioxolan-2,8'(5'H)-2H-2,4a-methanonaphthalene]), Timberol (1-(2,2,6-trimethylcyclohexyl)hexan-3-ol), iso-E-super, (2,3,8,8-tetramethyl-1,2,3,4,5,6,8-octahydro-2-naphthalenyl-methyl ketone), isobornyl acetate(2-exo-bornanyl acetate), Ylanate (2-tert-butylcyclohexyl acetate).

Particularly suitable floral fragrances are: Lilial (2-methyl-3-(4-tert-butylphenyl)propanal), Hedione (methyl(3-oxo-2-pentyl-cyclopentyl)acetate), Mayol (4-isopropyl-cyclohexyl)methanol), linalool (3,7-dimethyl-1,6-octadien-3-ol), dihydromyrcenol (2,6-dimethyl-7-octen-2-ol), citronellol (3,7-dimethyl-6-octen-1-ol), phenoxanol (3-methyl-5-phenyl-pentanol), 2-phenylethyl alcohol, hydroxycitronellal (3,7-dimethyl-7-hydroxyoctan-1-al), alpha-ionone (4-(2,6,6-trimethyl-cyclohex-2-enyl)-but-3-en-2-one).

The combination of compounds of formula (I) with the aforementioned preferred woody fragrances leads to brighter, radiant and clean odor impressions. The mixtures advantageously have a more natural and fresher effect.

The combination of compounds of formula (I) with the aforementioned preferred floral fragrances leads to particularly advantageous freshness and radiation. Furthermore, the floral aspects are perceived as more rounded through combination with one or a plurality of compounds of formula (I). Corresponding mixtures have a more intense and more harmonious odor.

According to another, preferred aspect of the present invention, the or one (further) is or two, three, a plurality of (further) or all of the further fragrance or flavoring materials according to ingredient (b) are green-fruity fragrances. Preferred green-fruity fragrances are: vertral (octahydro-1H-4,7-methanoindene-5-carbaldehyde), cis-3-hexen-1-ol, beta-damascone (1-(2,6,6-trimethyl-cyclohex-2-enyl)-buten-1-one), vertocitral (2,4-dimethylcyclohex-3-en-1-carbaldehyde), cyclogalbanate (allyl(cyclohexyloxy acetate), hexyl acetate.

The combination of these fragrances with compounds of formula (I) leads mainly to a rounder and softer odor. Moreover, addition of one or a plurality of compounds of formula (I) gives a certain brightness and imparts an impression of natural radiation.

According to another, preferred aspect of the present invention the or one (further) is or two, three, a plurality of (further) or all of the further fragrance or flavoring materials according to ingredient (b) are spicy-balsamic fragrances. Preferred spicy-balsamic fragrances are: eugenol (2-methoxy-4-allylphenol), coumarin (2H-1-benzopyran-2-one), anisaldehyde (4-methoxybenzaldehyde), amyl cinnamaldehyde (2-phenyl-3-phenyl-2-propenal), isoamylsalicylate (salicylic acid-3-methylbutyl ester) and cinnamon alcohol (3-phenyl-2-propen-1-ol).

The combination of these fragrances with compounds of formula (I) leads to particular freshness and naturalness. The mixtures have a more harmonious and more radiant effect.

In mixtures with further fragrances, the compounds of formula (I) are advantageously able, even in small dosages, to enhance the intensity of a fragrance mixture and to round off and harmonize the overall impression of the fragrance mixture especially in olfactory terms and give the mixture more radiance and naturalness.

For a fragrance and/or flavoring material mixture according to the invention (as described above), according to a preferred embodiment, the total amount of compounds of formula (I) is in the range from 0.00001 through 99.9 wt %, preferably in the range from 0.001 through 70 wt %, particularly preferably in the range from 0.01 through 50 wt %, relative to the total weight of the fragrance or flavoring material mixture, and/or the weight ratio of the total amount of ingredient (a) to the total amount of ingredient (b) in the fragrance or flavoring material mixture is in the range from 1:100 000 through 10:1, preferably in the range from 1:10 000 through 5:1, in particular in the range from 1:1000 through 2:1.

In particular for the case when the compounds of formula (I) are to be used according to the invention or a corresponding mixture is used or is to be used to give a fragrance and/or flavoring material mixture or composition (as described below) more radiation, roundness and/or harmony and/or to intensify certain notes, the total amount of ingredient (a) according to a preferred embodiment of the present invention is in the range from 0.01 through 5 wt %, preferably in the range from 0.1 through 2 wt %, relative to the total weight of the mixture or composition.

Depending on the desired use, it may be advantageous and accordingly preferable according to the invention to select the total amount of ingredient (a) so that depending on the further constituents of the respective mixture or composition, the aforementioned intrinsic odor and/or taste notes of the compound(s) of formula (I) are not (yet) imparted, but preferably one, a plurality of or all of the other positive properties (as described herein) become effective.

The compounds of formula (I) to be used according to the invention or corresponding mixtures thereof or a fragrance and/or flavoring material mixture according to the invention (as described above) can advantageously also be used for perfuming and/or flavoring certain articles or a constituent of said articles. In particular, a fragrance and/or flavoring material mixture according to the invention, preferably a fragrance and/or flavoring material mixture designated herein as preferable, can be used in the context of the present invention as constituent of a perfumed and/or flavored article.

Accordingly the present invention also relates to a perfumed and/or flavored article that comprises a fragrance and/or flavoring material mixture according to the invention (as described herein).

In an article according to the invention, preferably a total amount of compound(s) of formula (I) is contained that is sufficient to impart, to modify and/or to intensify an odor and/or taste note of the musk type, in particular radiant-musky, exalting and/or (softly) woody. Particularly preferably, the total amount of compound(s) of formula (I) is sufficient to attain one, a plurality of or all of the advantages described herein, that are to be achieved by the compounds or mixtures to be used according to the invention.

Regarding the compounds of formula (I) or mixtures thereof that are preferably contained and the further fragrances that are preferably contained, the foregoing applies correspondingly. Accordingly, an article according to the invention preferably comprises a fragrance and/or flavoring material mixture according to the invention that is designated herein as preferable according to the invention. The fragrance and/or flavoring material mixture according to the invention (that is contained) in its turn preferably comprises or consists of those fragrance and/or flavoring materials that are designated herein as preferred compounds of formula (I) according to the invention or as further fragrances that are preferably to be used (see in particular ingredient (b)). The foregoing statements regarding preferred amounts or weight ratios apply correspondingly.

According to one embodiment of the present invention, an article according to the invention is a composition of fragrance and/or flavoring materials.

Preferred substances that are contained or can be contained as further substances, preferably as further fragrances (in addition to compounds of formula (I)), in an article according to the invention, a fragrance and/or flavoring material composition according to the invention or in a fragrance and/or flavoring material mixture according to the invention, in the context of the present invention, can be found for example in S. Arctander, Perfume and Flavor Materials, Vol. I and II, Montclair, N.J. 1969, self-published, or K. Bauer et al., Common Fragrance and Flavor Materials, 4th Edition, Wiley-VCH, Weinheim 2001.

In detail, the following may be mentioned:

Extracts of natural raw materials such as essential oils, concretes, absolutes, resins, resinoids, balsams and tinctures, e.g. ambergris tincture; amyris oil; angelica seed oil; angelica root oil; anise oil; valerian oil; basil oil; tree moss absolute; bay oil; mugwort oil; gum benzoin; bergamot oil; beeswax absolute; birch tar oil; bitter almond oil; savory oil; buchu leaf oil; cabreuva oil; cade oil; calamus oil; camphor oil; cananga oil; cardamom oil; cascarilla oil; cassia oil; cassie absolute; castoreum absolute; cedar leaf oil; cedar wood oil; cistus oil; citronellol; lemon oil; copaiba balsam; copaiba balsam oil; coriander oil; costus root oil; cumin oil; cypress oil; davana oil; dill oil; dill seed oil; eau de brouts absolute; oak moss absolute; elemi oil; tarragon oil; eucalyptus-citriodora oil; eucalyptus oil; fennel oil; spruce needle oil; galbanum oil; galbanum resin; geranium oil; grapefruit oil; guaiac wood oil; gurjun balsam; gurjun balsam oil; helichrysum absolute; helichrysum oil; ginger oil; iris root absolute; iris root oil; jasmine absolute; calamus oil; chamomile oil blue; chamomile oil Roman; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil pressed; linaloe oil; Litsea cubeba oil; bay leaf oil; mace oil; marjoram oil; mandarin oil; massoy bark oil; mimosa absolute; ambrette seed oil; musk tincture; clary sage oil; nutmeg oil; myrrh absolute; myrrh oil; myrtle oil; clove leaf oil; clove blossom oil; neroli oil; olibanum absolute; olibanum oil; opopanax oil; orange blossom absolute; orange oil; origanum oil; palmarosa oil; patchouli oil; perilla oil; Peru balsam oil; parsley leaf oil; parsley seed oil; petitgrain oil; peppermint oil; pepper oil; pimento oil; pine oil; poley oil; rose absolute; rosewood oil; rose oil; rosemary oil; Dalmatian sage oil; Spanish sage oil; sandalwood oil; celery seed oil; spike lavender oil; star anise oil; styrax oil; tagetes oil; fir needle oil; tea tree oil; turpentine oil; thyme oil; tolu balsam; tonka absolute; tuberose absolute; vanilla extract; violet leaf absolute; verbena oil; vetiver oil; juniper berry oil; wine lees oil; wormwood oil; wintergreen oil; ylang-ylang oil; hyssop oil; civet absolute; cinnamon leaf oil; cinnamon bark oil and fractions thereof, or ingredients isolated therefrom;

Individual Fragrances from the Group of hydrocarbons, e.g. 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

of aliphatic alcohols, e.g. hexanol; octanol; 3-octanol; 2,6-dimethylheptanol; 2-methyl-2-heptanol; 2-methyl-2-octanol; (E)-2-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

of aliphatic aldehydes and acetals thereof, e.g. hexanal; heptanal; octanal; nonanal; decanal; undecanal; dodecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanaldiethylacetal; 1,1-dimethoxy-2,2,5-trimethyl-4-hexene; citronellyloxyacetaldehyde; 1-(1-methoxy-propoxy)-(E/Z)-3-hexene;

of aliphatic ketones and oximes thereof, e.g. 2-heptanone; 2-octanone; 3-octanone; 2-nonanone; 5-methyl-3-heptanone; 5-methyl-3-heptanone-oxime; 2,4,4,7-tetramethyl-6-octen-3-one; 6-methyl-5-hepten-2-one;

of aliphatic sulfur-containing compounds, e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

of aliphatic nitriles, e.g. 2-nonenoic acid nitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile;

of esters of aliphatic carboxylic acids, e.g. (E)- and (Z)-3-hexenyl formate; ethyl acetoacetate; isoamyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3- hexenyl-isobutyrate; hexylcrotonate; ethyl isovalerate; ethyl-2-methylpentanoate; ethylhexanoate; allylhexanoate; ethyl-heptanoate; allylheptanoate; ethyloctanoate; ethyl-(E,Z)-2,4-decadienoate; methyl-2-octinate; methyl-2-noninate; allyl-2-isoamyloxyacetate; methyl-3,7-dimethyl-2,6-octadienoate; 4-methyl-2-pentyl-crotonate;

of acyclic terpene alcohols, e.g. geraniol; nerol; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol, 2,6-dimethyl-2,5,7-octatrien-1-ol; and formates, acetates, propionates, isobutyrates, butyrates, isovalerates, pentanoates, hexanoates, crotonates, tiglinates and 3-methyl-2-butenoates thereof;

of acyclic terpene aldehydes and ketones, e.g. citronellal; 7-methoxy-3,7-dimethyloctanal; 2,6,10-trimethyl-9-undecenal; geranylacetone; and the dimethyl and diethyl acetals of geranial, neral;

of cyclic terpene alcohols, e.g. menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiol; and formates, acetates, propionates, isobutyrates, butyrates, isovalerates, pentanoates, hexanoates, crotonates, tiglinates and 3-methyl-2-butenoates thereof;

of cyclic terpene aldehydes and ketones, e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethyl-ionone; alpha-irone; beta-damascenone; 1-(2,4,4-trimethyl-2-cyclohexen-1-yl)-2-buten-1-one; 1,3,4,6,7,8a-hexahydro-1,1,5,5-tetramethyl-2H-2,4a-methano-naphthalen-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedar wood oil (methylcedryl ketone);

of cyclic alcohols, e.g. 4-tert.-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

of cycloaliphatic alcohols, e.g. alpha-3,3-trimethylcyclo-hexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

of cyclic and cycloaliphatic ethers, e.g. cineol; cedrylmethyl ether; cyclododecylmethyl ether; 1,1-dimethoxycyclododecane; (ethoxymethoxy)cyclododecane; alpha-cedrenepoxide; 3a,6,6,9a-tetramethyldodecahydro-naphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

of cyclic and macrocyclic ketones, e.g. 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone;

of cycloaliphatic aldehydes, e.g. 2-methyl-4-(2,2,6-trimethyl-cyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

of cycloaliphatic ketones, e.g. 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenylmethyl ketone; methyl-2,6,10-trimethyl-2,5,9-cyclododecatrienyl ketone; tert.-butyl-(2,4-dimethyl-3-cyclohexen-1-yl)ketone;

of esters of cyclic alcohols, e.g. 2-tert-butylcyclohexyl acetate; 4-tert-butylcyclohexyl acetate; 2-tert-pentylcyclohexyl acetate; 4-tert-pentyl-cyclohexyl acetate; 3,3,5-trimethylcyclohexyl acetate; decahydro-2-naphthyl acetate; 2-cyclo-pentylcyclopentylcrotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5, or 6-indenyl acetate; 4,7-methano-3a,4,5,6,7,7a-hexahydro-5, or 6-indenyl-propionate; 4,7-methano-3a,4,5,6,7,7a-hexahydro-5, or 6-indenylisobutyrate; 4,7-methanooctahydro-5, or 6-indenyl acetate;

of esters of cycloaliphatic alcohols, e.g. 1-cyclohexylethylcrotonate;

of esters of cycloaliphatic carboxylic acids, e.g. allyl-3-cyclohexyl propionate; allylcyclohexyloxyacetate; cis- and trans-methyldihydrojasmonate; cis- and trans-methyljasmonate; methyl-2-hexyl-3-oxocyclopentane carboxylate; ethyl-2-ethyl-6,6-dimethyl-2-cyclohexenecarboxylate; ethyl-2,3,6,6-tetramethyl-2-cyclohexene-carboxylate; ethyl-2-methyl-1,3-dioxolane-2-acetate;

of araliphatic alcohols, e.g. benzyl alcohol; 1-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-prop en-1-ol; 4-methoxybenzyl alcohol; 1-(4-isopropylphenyl)ethanol;

of esters of araliphatic alcohols and aliphatic carboxylic acids, e.g. benzyl acetate; benzyl propionate; benzyl isobutyrate; benzyl isovalerate; 2-phenylethyl acetate; 2-phenylethylpropionate; 2-phenylethylisobutyrate; 2-phenylethylisovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethylisobutyrate; 4-methoxybenzyl acetate;

of araliphatic ethers, e.g. 2-phenylethylmethyl ether; 2-phenylethyl-isoamyl ether; 2-phenylethyl-1-ethoxyethyl ether; phenylacetaldehyde-dimethylacetal; phenylacetaldehyde-diethylacetal; hydratropa aldehyde dimethylacetal; phenylacetaldehyde-glycerolacetal; 2,4,6-trimethyl-4-phenyl-1,3-dioxane; 4,4a,5,9b-tetra-hydroindeno[1,2-d]-m-dioxin; 4,4a,5,9b-tetrahydro-2,4-dimethylindeno[1,2-d]-m-dioxin;

of aromatic and araliphatic aldehydes, e.g. benzaldehyde; phenylacetaldehyde; 3-phenylpropanal; hydratropa aldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-isobutylphenyl)propanal; 3-(4-tert.-butyl-phenyl)propanal; cinnamaldehyde; alpha-butyl cinnamaldehyde; alpha-hexyl cinnamaldehyde;

3-methyl-5-phenylpentanal; 4-methoxybenzaldehyde; 4-hydroxy-3-methoxybenzaldehyde; 4-hydroxy-3-ethoxybenzaldehyde; 3,4-methylene dioxybenzaldehyde; 3,4-dimethoxybenzaldehyde; 2-methyl-3-(4-methoxyphenyl)propanal; 2-methyl-3-(4-methylene dioxyphenyl)propanal;

of aromatic and araliphatic ketones, e.g. acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanylmethyl ketone; 6-tert.-butyl-1,1-dimethyl-4-indanylmethyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

of aromatic and araliphatic carboxylic acids and esters thereof, e.g. benzoic acid; phenylacetic acid; methylbenzoate; ethylbenzoate; hexylbenzoate; benzylbenzoate; methylphenyl acetate; ethylphenyl acetate; geranylphenyl acetate; phenylethyl-phenyl acetate; methylcinnamate; ethylcinnamate; benzylcinnamate; phenylethylcinnamate; cinnamylcinnamate; allylphenoxyacetate; methylsalicylate; hexylsalicylate; cyclohexylsalicylate; cis-3-hexenylsalicylate; benzylsalicylate; phenylethylsalicylate; methyl-2,4-dihydroxy-3,6-dimethylbenzoate; ethyl-3-phenylglycidate; ethyl-3-methyl-3-phenylglycidate;

of nitrogen-containing aromatic compounds, e.g. 2,4,6-trinitro-1,3-dimethyl-5-tert.-butylbenzene; 3,5-dinitro-2,6-dimethyl-4-tert.-butylacetophenone; cinnamic acid nitrile; 3-methyl-5-phenyl-2-pentenoic acid nitrile; 3-methyl-5-phenylpentanoic acid nitrile; methylanthranilate; methyl-N-methylanthranilate; Schiff s bases of methylanthranilate with 7-hydroxy-3,7-dimethyloctanal, 2-methyl-3-(4-tert.-butylphenyl)propanal or 2,4-dimethyl-3-cyclohexenecarbaldehyde; 6-isopropyl-quinoline; 6-isobutylquinoline; 6-sec.-butylquinoline; 2-(3-phenylpropyl)pyridine; indole; skatole; 2-methoxy-3-isopropylpyrazine; 2-isobutyl-3-methoxypyrazine;

of phenols, phenyl ethers and phenyl esters, e.g. estragole; anethole; eugenylmethyl ether; isoeugenol; isoeugenylmethyl ether; thymol; carvacrol; diphenyl ether; beta-naphthylmethyl ether; beta-naphthylethyl ether; beta-naphthylisobutyl ether; 1,4-dimethoxybenzene; eugenyl acetate; 2-methoxy-4-methylphenol; 2-ethoxy-5-(1-propenyl)phenol; p-cresylphenyl acetate;

of heterocyclic compounds, e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

of lactones, e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,12-dodecanedioate; ethylene-1,13-tridecanedioate; 2,3-dihydrocoumarin; octahydrocoumarin.

A fragrance and/or flavoring material mixture according to the invention or a fragrance and/or flavoring material composition according to the invention or an article according to the invention is produced, according to a preferred embodiment, by providing ingredient (a) (as described above) or a mixture of ingredient (a) with an (optional) further ingredient (c) and optionally further ingredients, optionally consisting of substances additionally contained in a mixture or composition according to the invention, and mixing with one or a plurality of further fragrance and/or flavoring materials (see ingredient (b)). Ingredient (a) is preferably used in a total amount that is sufficient to impart, to modify and/or to intensify an odor and/or a taste note of the type described above in the finished mixture or composition or in the finished article. Moreover, the foregoing regarding preferred amounts and weight ratios applies correspondingly.

Fragrance and/or flavoring material compositions or mixtures according to the invention can be in liquid form, undiluted or diluted with a solvent and can be used optionally for perfuming or flavoring. Suitable solvents for this are e.g. ethanol, isopropanol, diethylene glycol monoethyl ether, glycerol, propylene glycol, 1,2-butylene glycol, dipropylene glycol, diethyl phthalate, triethyl citrate, isopropyl myristate and triacetin.

Moreover, fragrance and/or flavoring material compositions or mixtures according to the invention can be adsorbed on a carrier, which provides both fine distribution of the fragrance and/or flavoring materials in the product, and also controlled release during use. These carriers can be porous inorganic materials such as light sulfate, silica gels, zeolites, gypsums, clays, clay granules, gas concrete etc. or organic materials such as wood, cellulose-based materials, sugars, dextrins (e.g. maltodextrin) or plastics such as PVC, polyvinyl acetates or polyurethanes. The combination of composition or mixture according to the invention and carrier is an (example of) article according to the invention.

In particular, fragrance and/or flavoring material compositions according to the invention can also be in microencapsulated or spray-dried form, as inclusion complexes or as extrusion products and in this form can optionally be added in their turn to a (further) product or article that is to be perfumed and/or flavored.

Optionally, the properties of the compositions according to the invention can be further optimized by so-called "coating" with suitable materials with a view to a more targeted release of fragrance, for which preferably wax-like plastics are used, e.g. polyvinyl alcohol. The resultant products in their turn represent articles according to the invention.

The microencapsulation of the fragrance and/or flavoring material compositions according to the invention can take place for example by the so-called coacervation process using encapsulating materials, e.g. polyurethane-like substances or soft gelatin. The spray-dried fragrance and/or flavoring material compositions can be produced for example by spray-drying an emulsion or dispersion containing the fragrance and/or flavoring material composition, wherein modified starches, proteins, dextrin and vegetable gums can be used as carriers. Inclusion complexes can be produced for example by introducing dispersions of the fragrance or flavoring material composition and cyclodextrins or urea derivatives into a suitable solvent, e.g. water. Extrusion products can be obtained by melting the fragrance and/or flavoring material compositions with a suitable wax-like substance and by extrusion followed by solidification, optionally in a suitable solvent, e.g. isopropanol.

Fragrance and/or flavoring material compositions or fragrance and/or flavoring material mixtures, as described herein in each case, can be used in concentrated form, in solutions or in modified form described above, in particular for the production of (perfumed) articles according to the invention, e.g. perfume extracts, eaux de parfum, eaux de toilette, shaving lotions, eaux de Cologne, pre-shave products, splash Colognes and perfumed tissue wipes, and for the perfuming of acidic, alkaline and neutral cleaning agents, e.g. floor cleaners, window cleaners, washing-up liquids, bath and sanitary cleaners, scouring liquids, solid and liquid lavatory cleaners, powder and foam carpet cleaners, fabric fresheners, ironing aids, liquid detergents, powder detergents, washing pretreatment agents such as bleach, soaking agents and stain removers, fabric softeners, washing soaps, washing tablets, disinfectants, surface disinfectants and air fresheners in liquid or gel form or applied on a solid carrier, aerosol sprays, waxes and polishes such as furniture polishes, floor waxes, shoe creams and body-care products, e.g. solid and liquid soaps, shower gels, shampoos, shaving soaps, shaving foams, bath oils, cosmetic emulsions of the oil-in-water, water-in-oil and water-in-oil-in-water type, e.g. skin creams and lotions, face creams and lotions, sunscreen creams and lotions, after-sun creams and lotions, hand creams and lotions, foot creams and lotions, depilatory creams and lotions, after-shave creams and lotions, tanning creams and lotions, hair care products, e.g. hair sprays, hair gels, fixing hair lotions, hair rinses, permanent and semi-permanent hair coloring agents, hair shaping agents such as cold permanent waves and hair straightening agents, hair lotions, hair creams and lotions, deodorants and antiperspirants e.g. underarm sprays, roll-ons, deodorant sticks, deodorant creams, products of decorative cosmetics, e.g. eye shadow, nail varnishes, make-up, lipsticks, mascara, as well as candles, lamp oils, joss sticks, insecticides, repellents and propellants.

Accordingly, an article according to the invention (as described herein) is preferably selected from the group consisting of: perfume extracts, eaux de parfum, eaux de toilette, shaving lotions, eaux de Cologne, pre-shave products, splash Colognes, perfumed tissue wipes, acidic, alkaline and neutral cleaning agents, fabric fresheners, ironing aids, liquid detergents, powder detergents, washing pretreatment agents, fabric softeners, washing soaps, washing tablets, disinfectants, surface disinfectants, air fresheners, aerosol sprays, waxes and polishes, body-care products, hand creams and lotions, foot creams and lotions, depilatory creams and lotions, after-shave creams and lotions, tanning creams and lotions, hair care products, deodorants and antiperspirants, products of decorative cosmetics, candles, lamp oils, joss sticks, insecticides, repellents and propellants.

The compounds of formula (I) to be used according to the invention or corresponding mixtures thereof, fragrance and/or flavoring material mixtures according to the invention or fragrance and/or flavoring material compositions according to the invention can (in their turn) be incorporated in (further) articles that are flavored or are to be flavored, in particular in preparations used for nutrition, for oral hygiene or for pleasure. Such preparations are in their turn articles according to the invention (as described herein).

Preparations used for nutrition or for pleasure are for example baked products (e.g. bread, biscuits, cakes, other pastries), confectionery (e.g. chocolates, chocolate bars, other bar products, fruit gums, boiled sweets and toffees, chewing gum), alcoholic or non-alcoholic beverages (e.g. coffee, tea, wine, wine-containing beverages, beer, beer-containing beverages, liqueurs, spirits, brandies, fruit-containing lemonades, isotonic beverages, refreshing beverages, nectars, fruit and vegetable juices, fruit or vegetable juice preparations), instant beverages (e.g. instant cocoa beverages, instant tea beverages, instant coffee beverages), meat products (e.g. ham, sausage or raw-sausage preparations, spiced or marinated fresh or salted meat products), eggs or egg products (dried egg, egg white, egg yolk), cereal products (e.g. breakfast cereals, muesli bars, prefermented finished rice products), milk products (e.g. milk drinks, milk ice, yoghurt, kefir, fresh cheese, soft cheese, hard cheese, dry powdered milk, whey, butter, buttermilk, partially or fully hydrolyzed lactoprotein-containing products), products from soya protein or other soybean fractions (e.g. soya milk and products prepared therefrom, preparations containing soya lecithin, fermented products such as tofu or tempeh or products prepared therefrom, soy sauces), fruit preparations (e.g. jams, fruit ice, fruit sauces, fruit fillings), vegetable preparations (e.g. ketchup, sauces, dried vegetables, deep-frozen vegetables, prefermented vegetables, vegetables pickled in vinegar, preserved vegetables), nibbles (e.g. baked or fried potato chips or potato dough products, bread dough products, maize- or peanut-based extruded products), fat- and oil-based products or emulsions thereof (e.g. mayonnaise, remoulade, dressings, spice preparations), other ready-meals and soups (e.g. dried soups, instant soups, prefermented soups), spices, spice mixtures and in particular seasonings, which for example find application in the snack area. After incorporation of the compounds to be used according to the invention, the corresponding mixtures, fragrance and/or flavoring material mixtures according to the invention or fragrance and/or flavoring material compositions according to the invention, these preparations are preparations according to the invention (as preferred examples of articles according to the invention).

Preparations according to the invention can for example be in the form of semi-finished products or as spice mixture.

Preparations according to the invention can serve in particular as semi-finished products for making further preparations used for nutrition or for pleasure, in particular in spray-dried form. Preparations according to the invention can also be in the form of capsules, tablets (uncoated and coated tablets, e.g. with enteric coatings), sugar-coated pills, granules, pellets, mixtures of solids, dispersions in liquid phases, as emulsions, as powder, as solutions, as pastes or as other preparations that can be swallowed or chewed as food supplements.

Preparations according to the invention used for oral hygiene are in particular oral and/or dental hygiene products such as toothpastes, dental gels, tooth powders, mouthwash, chewing gum and other oral hygiene products.

Other usual active substances, bases, excipients and additives for preparations according to the invention used for nutrition, oral hygiene or pleasure can be contained in amounts from 5 through 99.999999 wt %, preferably 10 through 80 wt %, relative to the total weight of the preparation. Moreover, the preparations can have water in an amount of up to 99.999999 wt %, preferably 5 through 80 wt %, relative to the total weight of the preparation.

Preparations according to the invention are produced according to a preferred embodiment by incorporating a compound of formula (I) to be used according to the invention or a mixture of various compounds of formula (I) (as described herein) or mixtures or compositions described above, as substance, as solution (e.g. in ethanol, water or 1,2-propylene glycol) or in the form of a mixture with a solid or liquid carrier (e.g. maltodextrin, starch, silica gel), optionally with other flavorings or flavoring materials and/or fragrances and optionally (further) excipients and/or stabilizers (e.g. natural or artificial polysaccharides and/or vegetable gums such as modified starches or gum arabic) in a base preparation used for nutrition, oral hygiene or pleasure. Advantageously, preparations according to the invention in the form of solution and/or suspension or emulsion can also be transformed by spray-drying into a solid preparation according to the invention (semi-finished product).

The spray-dried solid preparations according to the invention (as an example of articles according to the invention) are particularly suitable as semi-finished products for making further preparations according to the invention. The spray-dried solid preparations according to the invention preferably contain 50 through 95 wt % of carriers, especially maltodextrin and/or starch, 5 through 40% of excipients, preferably natural or artificial polysaccharides and/or vegetable gums such as modified starch or gum arabic.

According to another preferred embodiment, for making preparations according to the invention, one or a plurality of compounds of formula (I) (as described above) and optionally further ingredients (preferably as described above) of the preparation according to the invention are first incorporated in emulsions, in liposomes, e.g. starting from phosphatidylcholine, in microspheres, in nanospheres or also in capsules, granules or extrudates from a matrix suitable for foodstuffs and semi-luxury foods, e.g. from starch, starch derivatives (e.g. modified starch), cellulose or cellulose derivatives (e.g. hydroxypropylcellulose), other polysaccharides (e.g. dextrin, alginate, curdlan, carrageenan, chitin, chitosan, pullulan), natural fats, natural waxes (e.g. beeswax, carnauba wax), from proteins, e.g. gelatin or other natural products (e.g. shellac). Depending on the matrix, the products can be obtained by spray-drying, spray-granulation, melt-granulation, coacervation, coagulation, extrusion, melt-extrusion, emulsion processes, coating or other suitable encapsulation processes and optionally a suitable combination of the aforementioned techniques.

In another preferred method of production for a preparation according to the invention, one or a plurality of compounds of formula (I) (as described above) and optionally further ingredients are first complexed with one or a plurality of complexing agents, for example with cyclodextrins or cyclodextrin derivatives, preferably α- or β-cyclodextrin, and are used in this complexed form.

A preparation according to the invention is particularly preferred in which the matrix is selected so that the compound(s) of formula (I) and optionally further fragrance and/or flavoring materials are released from the matrix with a delay, so that a long-lasting action is achieved. To that extent, a fat, wax, polysaccharide or protein matrix is particularly preferred.

As further constituents for preparations according to the invention used for nutrition or for pleasure, it is (also) possible to employ usual bases, excipients and additives for foodstuffs or semi-luxury foods, e.g. water, mixtures of fresh or processed, vegetable or animal bases or raw materials (e.g. raw, baked, dried, fermented, smoked and/or boiled meat, bones, cartilage, fish, vegetables, fruit, herbs, nuts, vegetable or fruit juices or pastes or mixtures thereof), digestible or non-digestible carbohydrates (e.g. sucrose, maltose, fructose, glucose, dextrins, amylose, amylopectin, inulin, xylan, cellulose, tagatose), sugar alcohols (e.g. sorbitol, erythritol), natural or hardened fats (e.g. tallow, lard, palm oil, coconut oil, hardened vegetable fat), oils (e.g. sunflower oil, peanut oil, corn oil, olive oil, fish oil, soya oil, sesame oil), fatty acids or salts thereof (e.g. potassium stearate), proteinogenic or non-proteinogenic amino acids and related compounds (e.g. γ-aminobutyric acid, taurine), peptides (e.g. glutathione), native or processed proteins (e.g. gelatin), enzymes (e.g. peptidases), nucleic acids, nucleotides, taste correctants for unpleasant taste impressions, further taste modulators for other, as a rule not unpleasant taste impressions, other taste modulating substances (e.g. inositol phosphate, nucleotides such as guanosine monophosphate, adenosine monophosphate or other substances such as sodium glutamate or 2-phenoxypropionic acid), emulsifiers (e.g. lecithins, diacylglycerols, gum arabic), stabilizers (e.g. carrageenan, alginate), preservatives (e.g. benzoic acid, sorbic acid), antioxidants (e.g. tocopherol, ascorbic acid), chelating agents (e.g. citric acid), organic or inorganic acidifying agents (e.g. malic acid, acetic acid, citric acid, tartaric acid, phosphoric acid), bitter substances (e.g. quinine, caffeine, limonin, amarogentin, humulones, lupulones, catechins, tannins), mineral salts (e.g. sodium chloride, potassium chloride, magnesium chloride, sodium phosphates), substances preventing enzymatic browning (e.g. sulfite, ascorbic acid), essential oils, plant extracts, natural or synthetic dyes or colored pigments (e.g. carotenoids, flavonoids, anthocyans, chlorophyll and derivatives thereof), spices, trigeminally active substances or plant extracts containing said trigeminally active substances, synthetic, natural or nature-identical flavoring materials or fragrances and odor correctants.

Dental hygiene products (as an example of preparations according to the invention used for oral hygiene) generally comprise an abrasive system (grinding or polishing agent), e.g. silicic acids, calcium carbonates, calcium phosphates, aluminum oxides and/or hydroxyapatites, surface-active substances, e.g. sodium lauryl sulfate, sodium lauryl sarcosinate and/or cocamidopropylbetaine, humectants, e.g. glycerol and/or sorbitol, thickeners, e.g. carboxymethylcellulose, polyethylene glycols, carrageenan and/or Laponite®, sweeteners, e.g. saccharin, taste correctants for unpleasant taste impressions, taste correctants for other, as a rule not unpleasant taste impressions, taste modulating substances (e.g. inositol phosphate, nucleotides such as guanosine monophosphate, adenosine monophosphate or other substances such as sodium glutamate or 2-phenoxypropionic acid), substances with a cooling effect, e.g. menthol, menthol derivatives (e.g. L-menthol, L-menthyllactate, L-menthylalkylcarbonates, menthone ketals, menthane carboxylic acid amides), 2,2,2-trialkylacetic acid amides (e.g. 2,2-diisopropylpropionic acid methyl amide), icilin and icilin derivatives, stabilizers and active substances, e.g. sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, cetylpyridinium chloride, aluminum lactate, potassium citrate, potassium nitrate, potassium chloride, strontium chloride, hydrogen peroxide, flavoring materials and/or sodium bicarbonate or odor correctants.

Chewing gums (as a further example of preparations according to the invention used for oral hygiene) generally comprise a chewing gum base, i.e. a gum base that becomes plastic during chewing, sugars of various kinds, sugar substitutes, other sweet-tasting substances, sugar alcohols, taste correctants for unpleasant taste impressions, other taste modulators for other, as a rule not unpleasant taste impressions, taste modulating substances (e.g. inositol phosphate, nucleotides such as guanosine monophosphate, adenosine monophosphate or other substances such as sodium glutamate or 2-phenoxypropionic acid), humectants, thickeners, emulsifiers, flavoring materials and stabilizers or odor correctants.

Preferably the preparations according to the invention can also contain a (further) flavoring composition, for rounding off and improving the taste and/or odor of the preparation. Suitable (additional) flavoring compositions contain for example synthetic, natural or nature-identical aromatic, fragrance and flavoring substances and suitable excipients and carriers.

As described above, in the context of the present invention, compounds of formula (I) and corresponding mixtures thereof are provided that are also novel over the prior art.

Accordingly, another aspect of the present invention relates to a compound of formula (I)

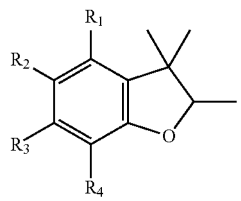

or a mixture consisting of two, three, four, five, six or a plurality of different compounds of formula (I), wherein for the residues of the compound of formula (I) or the residues of all compounds of formula (I), in each case independently of one another, the following applies:

$R_1$ denotes hydrogen, methyl, tert-butyl, acetyl, formyl or cyano, preferably hydrogen or methyl, $R_2$ denotes hydrogen, methyl, tert-butyl, formyl, acetyl or cyano, preferably formyl or acetyl, $R_3$ denotes hydrogen, methyl or tert-butyl, and $R_4$ denotes hydrogen, methyl, ethyl, propyl, isopropyl, butyl, sec-butyl, tert-butyl, isobutyl, formyl, acetyl or cyano, preferably methyl, ethyl, isopropyl or tert-butyl, preferably wherein for the residues of the compound of formula (I) or the residues of all compounds of formula (I), in each case independently of one another, the following applies:

$R_1$ denotes hydrogen, methyl, acetyl or formyl, preferably hydrogen or methyl, $R_2$ denotes methyl, formyl or acetyl, preferably formyl or acetyl, $R_3$ denotes hydrogen or methyl, and $R_4$ denotes methyl, ethyl, propyl, isopropyl, butyl, sec-butyl, tert-butyl or isobutyl, preferably methyl, ethyl, isopropyl or tert-butyl.

The compounds and mixtures described above and hereunder are compounds or mixtures that are preferably to be used in the context of the present invention.

A compound or mixture (as described above) is particularly preferred, wherein for the residues of the compound of formula (I) or the residues of all compounds of formula (I), in each case independently of one another, the following applies:

$R_1$ denotes hydrogen or methyl, $R_2$ denotes formyl or acetyl, $R_3$ denotes hydrogen or methyl, and $R_4$ denotes methyl, ethyl, isopropyl or tert-butyl.

A compound or mixture (as described above) is further preferred, wherein the compound of formula (I) or one, a plurality of or all compounds of formula (I) is selected, or in each case independently of one another are selected, from the group consisting of the following compounds 1 through 8, preferably from compounds 2, 4 and 5:

COMPOUND 1

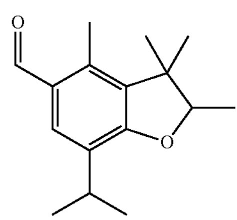

-continued

COMPOUND 2

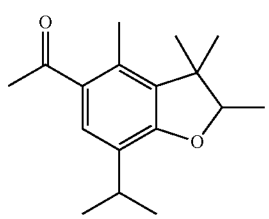

COMPOUND 3

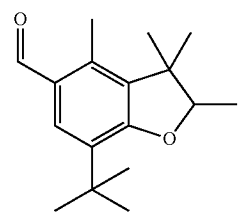

COMPOUND 4

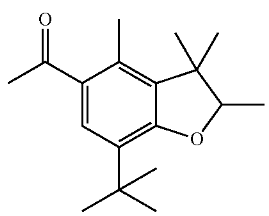

COMPOUND 5

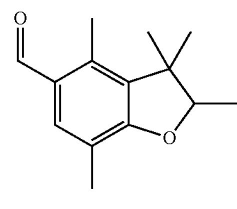

COMPOUND 6

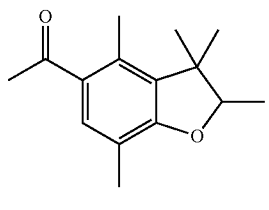

COMPOUND 7

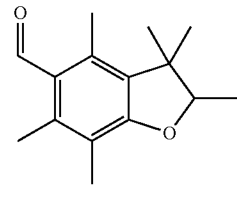

COMPOUND 8

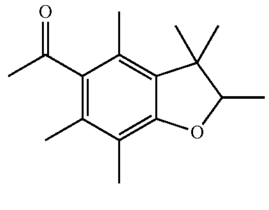

Another aspect of the present invention relates to a method of imparting, modifying and/or intensifying an odor and/or taste, preferably a musky and/or woody odor and/or taste, comprising the following step:

Contacting or mixing a sensorially effective amount of a compound of formula (I)

(I)

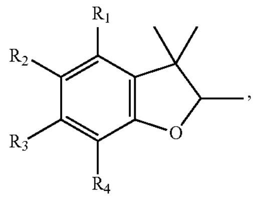

as defined above, of a mixture of two, three, four, five, six or a plurality of different compounds of formula (I), as defined above, or of a fragrance and/or flavoring material mixture according to the invention (as described herein)

with a product.

Preferred products are the articles or preparations described above that are preferred according to the invention.

Moreover, the foregoing applies correspondingly to selection of the compounds of formula (I), the composition of a fragrance and/or flavoring material mixture according to the invention and the preferred amounts and weight ratios.

In the context of the present invention, also the use of a compound of formula (I)

(I)

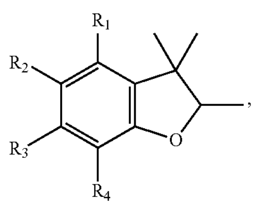

as defined above, of a mixture of two, three, four, five, six or a plurality of different compounds of formula (I), as defined above, or of a fragrance and/or flavoring material mixture according to the invention (as described herein), or of an article according to the invention (as described herein)

is described for providing (a) hair, (b) skin or (c) textile fibers with an—in particular musky—fragrance and/or taste (regarding further preferred odor or taste notes, see above).

Another aspect in connection with the present invention relates to the use of a compound of formula (I)

(I)

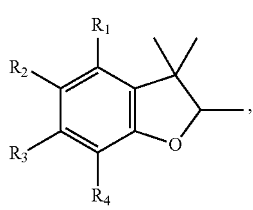

as defined above, of a mixture of two, three, four, five, six or a plurality of different compounds of formula (I), as defined above, or of a fragrance and/or flavoring material mixture according to the invention (as described herein)

as an agent for increasing the substantivity and/or retention of a fragrance mixture and/or as fixative and/or as an agent for increasing the odor of other fragrances perceived via a surfactant-containing aqueous solution.

In connection with the use for modifying and/or intensifying an odor and/or taste note, there is also the finding (according to the invention) that the compounds to be used according to the invention or the corresponding mixtures (as described above) can function particularly well as so-called boosters (intensifiers; enhancers). Accordingly, corresponding relevant uses of compounds of formula (I) are also to be considered to form part of the subject matter of the present invention.

The present invention is explained in more detail below, with examples. Unless stated otherwise, all data provided refer to weight.

EXAMPLES

Example 1

General Specification for Preparing Prenyl Ethers

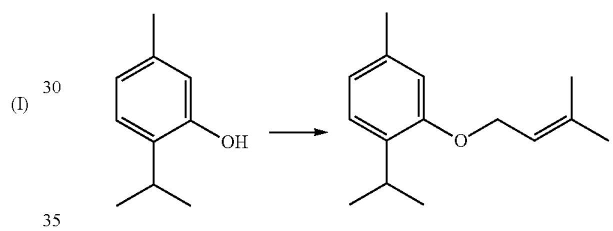

In a 500-ml stirred vessel, 60.1 g (0.4 mol) of thymol is added at room temperature to a solution of 52.3 g (80%, 0.4 mol) of prenyl chloride in 250 ml of N-methyl-2-pyrrolidone (NMP). Then 35.2 g of aqueous NaOH (50%, 0.44 mol) is added dropwise slowly with simultaneous ice cooling and on completion of addition it is heated to 40° C. and stirred for 2 hours. Then 250 ml of water is added to the mixture, it is neutralized with 2 M NaOH, and the phases are separated. The aqueous phase is extracted twice with 150 ml MtBE, the organic phases are combined, dried and concentrated by evaporation. The crude product (106 g) is fractionated on a 30 cm Vigreux column under vacuum.

When this was carried out, 54.1 g was obtained at 98% purity. This corresponds to a theoretical yield of 61% (b.p.: 95°-105° C./2 mbar).

Other prenyl ethers can be synthesized with good to very good yields according to this specification.

Example 2

General Specification for Preparing Dihydrobenzofurans

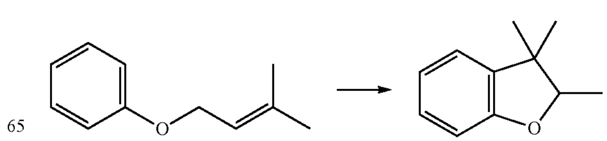

In a 250-ml stirred vessel, 121.7 g (0.75 mol) of prenyl phenyl ether with 0.84 g (15 mmol, 0.02 eq.) of powdered KOH is heated to 210° C., stifling continuously, and is kept at this temperature for 3 h. During this time, low-boiling fractions that form are removed by means of a water separator. After cooling to room temperature, the mixture is neutralized with saturated $NH_4Cl$ solution, MtBE is added, and the phases are separated. The aqueous phase is extracted once with MtBE. The combined organic phases are dried, concentrated by evaporation, and the crude product obtained (106.9 g) is fractionated on a 30 cm Vigreux column under vacuum.

When this was carried out, 47.9 g was obtained at 97% purity. This corresponds to a theoretical yield of 38% (b.p.: 56°-65° C./6 mbar).

Further dihydrobenzofurans can be synthesized with good to satisfactory yields according to this specification.

Example 3

General Specification for Preparing Acetyldihydrobenzofurans

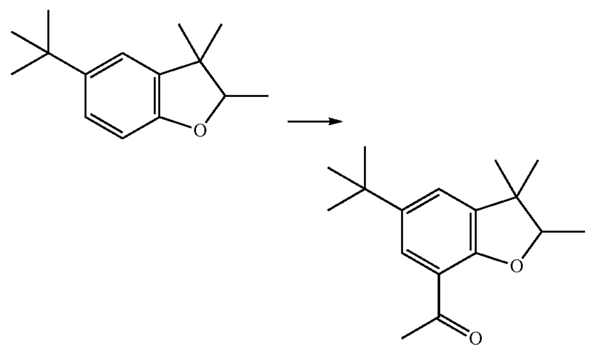

2.06 g (26.2 mmol, 1.05 eq.) of acetyl chloride is added to a solution of 4.00 g (30 mmol, 1.2 eq.) of aluminum chloride in 500 ml of dichloromethane under nitrogen at 0° C. Then 5.46 g of 5-tert.-butyl-2,3,3-trimethyl-2,3-dihydrobenzofuran is added dropwise at 0° C. and stirred for a further three hours. The mixture is poured onto ice, neutralized with 2 M NaOH, extracted once with dichloromethane, and the combined organic phases are dried and concentrated by evaporation. 10 g of ethanol is added to the crude product obtained (6.01 g, 60%), it is refluxed for 10 minutes, and the crystals that precipitate on cooling are filtered off with suction and dried under vacuum.

When this was carried out, 2.00 g was obtained at 97% purity. This corresponds to a theoretical yield of 31%.

Further acetyldihydrobenzofurans can be synthesized with good to satisfactory yields according to this specification.

Example 4

General Specification for Formylation of Dihydrobenzofurans

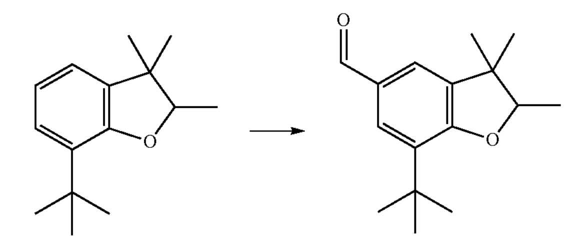 [SMILES: CC1Oc2c(C(C)(C)C)cccc2C1(C)C ; CC1Oc2c(C(C)(C)C)cc(C=O)cc2C1(C)C]

12.6 g of phosphoryl chloride (82.5 mmol, 1.6 eq.) is added dropwise under nitrogen at room temperature to a solution of 13.5 g (0.1 mol, 2.0 eq.) of N-methylformanilide in 150 ml toluene and is stirred for one hour at this temperature. After adding 10.9 g (50 mmol) of 7-tert.-butyl-2,3,3-trimethyl-2H-benzofuran it is heated to 80° C. and stirred for four hours at this temperature. Then 150 g of a 30% sodium acetate solution is added and it is refluxed for one hour. After cooling to room temperature and adding water and MtBE, the phases are separated, extracted once with MtBE, the organic phases are combined and dried. After concentrating by evaporation, the crude product thus obtained is separated from the bottom fraction by bulb-tube distillation (up to 110° C./0.1 mbar) and then purified by column chromatography (silica gel; cyclohexane/ethyl acetate=40/1).

When this was carried out, 6.13 g was obtained at 99% purity. This corresponds to a theoretical yield of 50%.

Further formylated dihydrobenzofurans can be synthesized with good to satisfactory yields according to this specification.

Example 5

General Specification for Cyanation of Formyl Dihydrobenzofurans

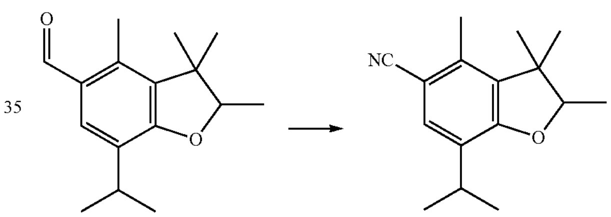

800 mg (20 mmol) of NaOH and 2.46 g (10 mmol) of 7-isopropyl-2,3,3,4-tetramethyl-2H-benzofuran-5-carbaldehyde are added at room temperature to a solution of 690 mg of hydroxylamine hydrochloride (10 mmol) in 40 ml water and stirred at 55° C. for 4 h. Then it is diluted at room temperature with water and MtBE, the phases are separated, the aqueous phase is extracted with MtBE, the organic phases are combined, dried, concentrated by evaporation and the crude product is filtered with cyclohexane/ethyl acetate on silica gel. The material thus obtained is recrystallized from 7 g of n-heptane.

When this was carried out, 1.06 g was obtained at 97% purity. This corresponds to a theoretical yield of 41%.

Further oximes can be synthesized with good to very good yields according to this specification.

1.02 g (3.90 mmol) of 7-isopropyl-2,3,3,4-tetramethyl-2H-benzofuran-5-carbaldehyde oximes (dissolved in 2 g acetic anhydride) is added slowly at 100° C. to a solution of 8.0 mg of copper sulfate pentahydrate (0.031 mmol) in 2.00 g of acetic anhydride. After 4 h the mixture is cooled to 0° C., quenched with water, MtBE is added, the phases are separated and the aqueous phase is extracted with MtBE. The combined organic phases are dried, concentrated by evaporation and the crude product thus obtained is purified chromatographically (silica gel; cyclohexane/ethyl acetate=5/1).

When this was carried out, 657 mg was obtained at 98% purity. This corresponds to a theoretical yield of 70%.

Further nitrile derivatives can be synthesized with good to very good yields according to this specification.

The spectroscopic data of some of the compounds prepared in the context of investigations carried out—in connection with the present invention—and corresponding intermediates were determined. Examples of the data are given below.

1-tert.-Butyl-4-(3-methylbut-2-enoxy)benzene

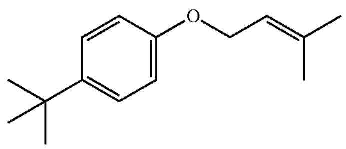 [SMILES: CC(C)=CCOc1ccc(C(C)(C)C)cc1]

$^1$H-NMR (400 MHz, $CDCl_3$): δ = 1.30 (s, 9H), 1.75-1.72 (m, 3H), 1.81-1.77 (m, 3H), 4.49 (d, J = 6.8 Hz, 2H), 5.50 (dddd, J = 6.8 Hz, J = 5.4 Hz, J = 2.8 Hz, J = 1.4 Hz, 1H), 6.89-6.81 (m, 2H), 7.34-7.24 (m, 2H) ppm.
$^{13}$C-NMR (100 MHz, $CDCl_3$): δ = 18.16 (q), 25.84 (q), 31.53 (q, q, q), 34.04 (s), 64.66 (t), 114.04 (d, d) 119.93 (d), 126.16 (d, d), 137.96 (s), 143.21 (s), 156.60 (s) ppm.
MS (EI): m/z (%) = 150 (26), 136 (11), 135 (100), 107 (12), 91 (10), 77 (6), 69 (22), 41 (42), 39 (9), 27 (6).

5-tert.-Butyl-2,3,3-trimethyl-2H-benzofuran

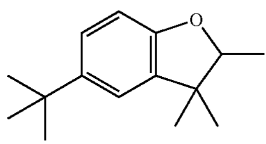 [SMILES: CC1Oc2ccc(C(C)(C)C)cc2C1(C)C]

$^1$H-NMR (400 MHz, $CDCl_3$): δ = 1.09 (s, 3H), 1.30 (s, 9H), 1.31 (s, 3H), 1.36 (d, J = 6.6 Hz, 3H), 4.36 (q, J = 6.6 Hz, 1H), 6.69 (dd, J = 8.3 Hz, J = 0.5 Hz, 1H), 7.09 (dd, J = 2.2 Hz, J = 0.4 Hz, 1H), 7.12 (dd, J = 8.3 Hz, J = 2.2 Hz, 1H) ppm.
$^{13}$C-NMR (100 MHz, $CDCl_3$): δ = 14.41 (q), 23.38 (q), 25.87 (q), 31.77 (q, q, q), 34.38 (s), 43.78 (s), 88.88 (d), 108.61 (d), 119.23 (d), 124.47 (d), 137.10 (s), 143.51 (s), 155.96 (s) ppm.
MS (EI): m/z (%) = 218 (23), 204 (16), 203 (100), 147 (15), 91 (9), 69 (7), 57 (30), 43 (8), 41 (25), 29 (10).

5-tert.-Butyl-2,3,3-trimethyl-3H-benzofuran

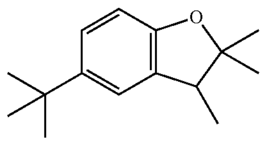 [SMILES: CC1c2cc(C(C)(C)C)ccc2OC1(C)C]

$^1$H-NMR (400 MHz, $CDCl_3$): δ = 1.23 (d, J = 7.2 Hz, 3H), 1.27 (s, 3H), 1.30 (s, 9H), 1.46 (s, 3H), 3.14 (q, J = 1.1 Hz, 1H), 6.62-6.65 (m, 1H), 7.10-7.13 (m, 2H) ppm.
$^{13}$C-NMR (100 MHz, $CDCl_3$): δ = 14.73 (q), 22.05 (q), 28.17 (q), 31.77 (q, q, q), 34.28 (s), 45.92 (d), 89.44 (s), 108.54 (d), 120.87 (d), 124.59 (d), 132.32 (s), 142.97 (s), 155.71 (s) ppm.

1-(5-tert.-Butyl-2,3,3-trimethyl-2H-benzofuran-7-yl)ethanone

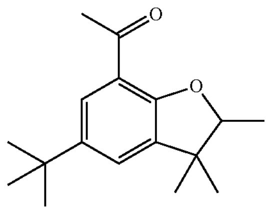 [SMILES: CC(=O)c1cc(C(C)(C)C)cc2c1OC(C)C2(C)C]

$^1$H-NMR (400 MHz, $CDCl_3$): δ = 1.12 (s, 3H), 1.31 (s, 9H), 1.33 (s, 3H), 1.41 (d, J = 6.6 Hz, 3H), 2.63 (s, 3H), 4.48 (q, J = 6.6 Hz, 1H), 7.26 (d, J = 2.2 Hz, IH), 7.71 (d, J = 2.2 Hz, 1H) ppm.
$^{13}$C-NMR (100 MHz, $CDCl_3$): δ = 14.71 (q), 23.36 (q), 26.29 (q), 31.15 (q), 31.56 (q, q, q), 34.49 (s), 43.21 (s), 89.91 (d), 119.86 (s), 124.07 (d), 124.58 (d), 139.49 (s), 143.60 (s), 156.86 (s), 197.47 (s) ppm.
MS (EI): m/z (%) = 260 (23), 246 (14), 245 (77), 189 (10), 128 (8), 115 (12), 91 (11), 57 (16), 43 (100), 41 (21).

1-tert.-Butyl-2-(3-methylbut-2-enoxy)benzene

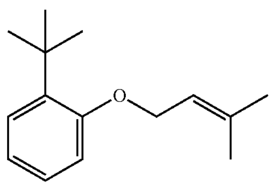 [SMILES: CC(C)=CCOc1ccccc1C(C)(C)C]

$^1$H-NMR (400 MHz, $CDCl_3$): δ = 1.38 (s, 9H), 1.72-1.74 (m, 3H), 1.77-1.81 (m, 3H), 4.54 (d, J = 6.5 Hz, 2H), 5.49-5.57 (m, 1H), 6.85-6.90 (m, 2H), 7.16 (ddd, J = 8.2 Hz, J = 7.3 Hz, J = 1.7 Hz, 1H), 7.27 (dd, J = 8.0 Hz, J = 1.8 Hz, 1H) ppm.
$^{13}$C-NMR (100 MHz, $CDCl_3$): δ = 18.23 (q), 25.73 (q), 29.76 (q, q, q), 34.82 (s), 64.85 (t), 112.34 (d), 120.07 (d), 120.35 (d), 126.53 (d), 126.87 (d), 136.65 (s), 138.33 (s), 157.75 (s) ppm.
MS (EI): m/z (%) = 150 (39), 136 (10), 135 (100), 107 (30), 91 (23), 77 (9), 69 (65), 41 (65), 39 (15), 27 (10).

7-tert.-Butyl-2,3,3-trimethyl-2H-benzofuran

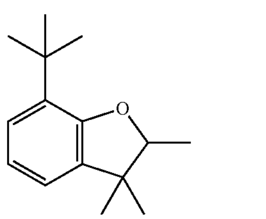 [SMILES: CC1Oc2c(C(C)(C)C)cccc2C1(C)C]

$^1$H-NMR (400 MHz, $CDCl_3$): δ = 1.08 (s, 3H), 1.28 (s, 3H), 1.35 (d, J = 6.6 Hz, 3H), 1.36 (s, 9H), 4.34 (q, J = 6.5 Hz, 1H), 6.81 (dd, J = 7.8 Hz, J = 7.3 Hz, 1H), 6.94 (dd, J = 7.3 Hz, J = 1.4 Hz, 1H), 7.06 (dd, J = 7.8 Hz, J = 1.4, 1H) ppm.
$^{13}$C-NMR (100 MHz, $CDCl_3$): δ = 14.68 (q), 23.05 (q), 26.36 (q), 29.29 (q, q, q), 34.10 (s), 43.18 (s), 87.94 (d), 120.06 (d), 120.11 (d), 124.42 (d), 132.98 (s), 137.91 (s), 156.28 (s) ppm.
MS (EI): m/z (%) = 218 (32), 204 (16), 203 (100), 161 (20), 147 (53), 115 (12), 91 (18), 57 (73), 41 (31), 29 (12).

-continued 7-tert.-Butyl-2,2,3-trimethyl-3H-benzofuran

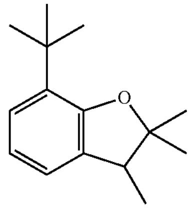 [SMILES: CC1c2cccc(C(C)(C)C)c2OC1(C)C]

$^1$H-NMR (400 MHz, $CDCl_3$): δ = 1.20 (d, J =1.1 Hz, 3H), 1.24 (s, 3H), 1.34 (s, 9H), 1.47 (s, 3H), 3.10 (q, J = 7.1 Hz, 1H), 6.78 (dd, J = 7.8 Hz, J = 7.3 Hz, 1H), 6.93-6.96 (m, 1H), 7.05 (dd, J = 7.8 Hz, J = 1.0 Hz, 1H) ppm.
$^{13}$C-NMR (100 MHz, $CDCl_3$): δ = 14.53 (q), 21.83 (q), 28.00 (q), 29.18 (q, q, q), 33.99 (s), 45.32 (d), 88.64 (s), 119.57 (d), 121.57 (d), 124.45 (d), 132.83 (s), 133.25 (s), 156.27 (s) ppm 1-(7-tert.-Butyl-2,3,3-trimethyl-2H-benzofuran-5-yl)ethanone

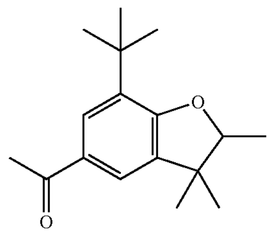 [SMILES: CC(=O)c1cc(C(C)(C)C)c2c(c1)C(C)(C)C(C)O2]

$^1$H-NMR (400 MHz, $CDCl_3$): δ = 1.12 (s, 3H), 1.32 (s, 3H), 1.38 (s, 9H), 1.38 (d, J = 6.5 Hz, 3H), 2.56 (s, 3H), 4.46 (q, J = 6.5 Hz, 1H), 7.60 (d, J = 1.9 Hz, 1H), 7.76 (d, J = 1.9 Hz, 1H) ppm.
$^{13}$C-NMR (100 MHz, $CDCl_3$): δ = 14.80 (q), 23.09 (q), 26.41 (q), 26.59 (q), 29.11 (q, q, q), 34.19 (s), 42.92 (s), 89.46 (d), 121.09 (d), 126.72 (d), 130.50 (s), 132.72 (s), 138.50 (s), 160.87 (s), 197.10 (s) ppm.
MS (EI): m/z (%) = 261 (7), 260 (34), 246 (19), 245 (100), 203 (15), 189 (29), 115 (8), 57 (11), 43 (77), 41 (12).

7-tert.-Butyl-2,3,3-trimethyl-2H-benzofuran-5-carbaldehyde

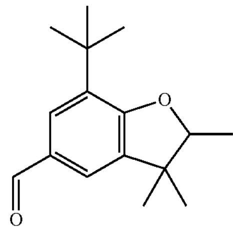 [SMILES: CC1Oc2c(C(C)(C)C)cc(C=O)cc2C1(C)C]

$^1$H-NMR (400 MHz, $CDCl_3$): δ = 1.13 (s, 3H), 1.33 (s, 3H), 1.38 (s, 9H), 1.38 (d, J = 6.6 Hz, 3H), 4.50 (q, J = 6.6 Hz, 1H), 7.53 (d, J = 1.7 Hz, 1H), 7.61 (d, J = 1.7 Hz, 1H), 9.83 (s, 1H) ppm.
$^{13}$C-NMR (100 MHz, $CDCl_3$): δ = 14.82 (q), 23.08 (q), 26.59 (q), 29.05 (q, q, q), 34.18 (s), 42.81 (s), 89.76 (d), 121.67 (d), 129.48 (d), 130.26 (s), 133.52 (s), 139.35 (s), 162.19 (s), 191.27 (d) ppm.
MS (EI): m/z (%) = 246 (36), 232 (17), 231 (100), 189 (17), 175 (34), 147 (13), 115 (9), 91 (10), 57 (19), 41 (10).

7-tert.-Butyl-2,3,3-trimethyl-2H-benzofuran-5-carbaldehyde oxime

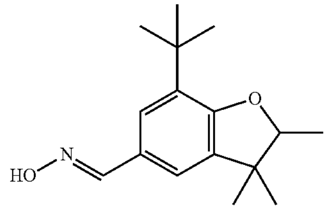 [SMILES: CC1Oc2c(C(C)(C)C)cc(/C=N/O)cc2C1(C)C]

$^1$H-NMR (400 MHz, $CDCl_3$): δ = 1.10 (s, 3H), 1.30 (s, 3H), 1.34-1.37 (m, 12H), 4.40 (q, J = 6.5 Hz, 1H), 7.22 (dd, J = 1.8 Hz, J = 0.4 Hz, 1H), 7.23 (dd, J = 1.8 Hz, J = 0.4 Hz, 1H), 7.61 (s, 1H), 8.05-8.13 (m, 1H) ppm.
$^{13}$C-NMR (100 MHz, $CDCl_3$): δ = 14.73 (q), 23.02 (q), 26.42 (q), 29.14 (q, q, q), 34.12 (s), 43.11 (s), 88.80 (d), 118.64 (d), 124.23 (s), 124.93 (d), 133.27 (s), 138.91 (s), 151.02 (d), 158.25 (s) ppm.
MS (EI): m/z (%) = 261 (59), 247 (16), 246 (100), 230 (15), 228 (36), 204 (16), 190 (48), 172 (18), 57 (24), 41 (16)

7-tert.-Butyl-2,3,3-trimethyl-2H-benzofuran-5-carbonitrile

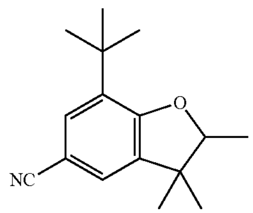 [SMILES: CC1Oc2c(C(C)(C)C)cc(C#N)cc2C1(C)C]

$^1$H-NMR (400 MHz, $CDCl_3$): δ = 1.11 (s, 3H), 1.30 (s, 3H), 1.34 (s, 9H), 1.37 (d, J = 6.6 Hz, 3H), 4.46 (q, J = 6.5 Hz, 1H), 7.21 (d, J = 1.7 Hz, 1H), 7.36 (d, J = 1.7 Hz, 1H) ppm.
$^{13}$C-NMR (100 MHz, $CDCl_3$): δ = 14.69 (q), 23.03 (q), 26.44 (q), 28.89 (q, q, q), 34.31 (s), 43.15 (s), 89.39 (d), 103.19 (s), 120.33 (s), 124.52 (d), 129.98 (d), 134.27 (s), 139.22 (s), 160.09 (s). ppm.
MS (EI): m/z (%) = 243 (27), 229 (17), 228 (100), 186 (17), 173 (6), 172 (48), 158 (9), 57 (10), 41 (6), 28 (10).

-continued 1-tert.-Butyl-3-(3-methylbut-2-enoxy)benzene

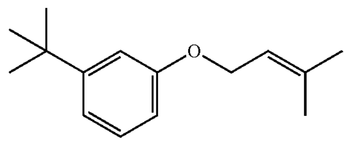 [SMILES: CC(C)=CCOc1cccc(C(C)(C)C)c1]

$^1$H-NMR (400 MHz, $CDCl_3$): δ = 1.30 (s, 9H), 1.72-1.75 (m, 3H), 1.78-1.82 (m, 3H), 4.50 (dt, J = 6.8 Hz, J = 0.8 Hz, 2H), 5.45-5.57 (m, 1H), 6.73 (ddd, J = 8.2 Hz, J = 2.4 Hz, J = 1.1 Hz, 1H), 6.93-7.01 (m, 2H), 7.17-7.26 (m, 1H) ppm.
$^{13}$C-NMR (100 MHz, $CDCl_3$): δ = 18.18 (q), 25.85 (q), 31.31 (q, q, q), 34.73 (s), 64.56 (t), 110.56 (d), 112.85 (d), 117.75 (d), 119.88 (d), 128.87 (d), 138.02 (s), 152.89 (s), 158.67 (s) ppm.
MS (EI): m/z (%) = 151 (5), 150 (50), 136 (10), 135 (100), 107 (18), 95 (5), 91 (7), 69 (31), 41 (31), 39 (5).

6-tert.-Butyl-2,3,3-trimethyl-2H-benzofuran

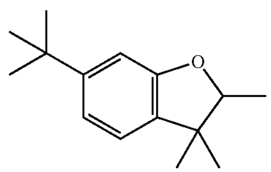 [SMILES: CC1Oc2cc(C(C)(C)C)ccc2C1(C)C]

$^1$H-NMR (400 MHz, $CDCl_3$): δ = 1.08 (s, 3H), 1.29 (s, 3H), 1.29 (s, 9H), 1.36 (d, J = 6.6 Hz, 3H), 4.37 (q, J = 6.6 Hz, 1H), 6.83 (dd, J = 1.7 Hz, J = 0.5 Hz, 1H), 6.90 (dd, J = 7.8 Hz, J = 1.7 Hz, 1H), 7.00 (dd, J = 7.8 Hz, J = 0.5 Hz, 1H) ppm.
$^{13}$C-NMR (100 MHz, $CDCl_3$): δ = 14.47 (q), 23.35 (q), 25.98 (q), 31.50 (q, q, q), 34.75 (s), 43.41 (s), 88.93 (d), 106.87 (d), 117.41 (d), 121.69 (d), 134.53 (s), 151.54 (s), 158.22 (s). ppm 1-(6-tert.-Butyl-2,3,3-trimethyl-2H-benzofuran-5-yl)ethanone

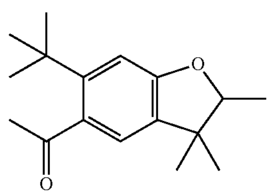 [SMILES: CC(=O)c1cc2c(cc1C(C)(C)C)OC(C)C2(C)C]

$^1$H-NMR (400 MHz, $CDCl_3$): δ = 1.09 (s, 3H), 1.30 (s, 3H), 1.35 (s, 9H), 1.37 (d, J = 6.6 Hz, 3H), 2.58 (s, 3H), 4.40 (q, J = 6.6 Hz, 1H), 6.88 (d, J = 0.4 Hz, 1H), 6.90 (d, J = 0.3 Hz, 1H) ppm.
$^{13}$C-NMR (100 MHz, $CDCl_3$): δ = 14.51 (q), 23.23 (q), 26.04 (q), 31.88 (q, q, q), 32.48 (q), 36.09 (s), 43.49 (s), 89.48 (d), 108.67 (d), 120.60 (d), 134.08 (s), 135.00 (s), 148.50 (s), 159.09 (s), 207.66 (s) ppm.
MS (EI): m/z (%) = 260 (13), 246 (17), 245 (100), 243 (5), 187 (5), 115 (8), 69 (6), 57 (8), 43 (41), 41 (8)

1-Isopropyl-2-(3-methylbut-2-enoxy)benzene

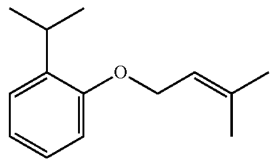

1H-NMR (400 MHz, $CDCl_3$): δ = 1.21 (d, J = 6.9 Hz, 6H), 1.71-1.75 (m, 3H), 1.76-1.82 (m, 3H), 3.35 (hept., J = 7.0 Hz, 1H), 4.52 (d, J = 6.4 Hz, 2H), 5.46-5.55 (m, 1H), 6.85 (dd, J = 8.1 Hz, J = 1.2 Hz, 1H), 6.91 (ddd, J = 7.5 Hz, J = 1.2 Hz, 1H), 7.13 (ddd, J = 8.2 Hz, J = 7.4 Hz, J = 1.8 Hz, 1H), 7.21 (dd, J = 7.5 Hz, J = 1.8 Hz, 1H) ppm.
$^{13}$C-NMR (100 MHz, $CDCl_3$): δ = 18.24 (q), 22.73 (q, q), 25.77 (q), 26.70 (d), 65.12 (t), 111.74 (d), 120.39 (d), 120.50 (d), 126.02 (d), 126.39 (d), 137.00 (s), 137.39 (s), 156.07 (s) ppm.
MS (EI): m/z (%) = 136 (47), 122 (9), 121 (100), 91 (23), 77 (12), 69 (52), 65 (9), 41 (60), 39 (15), 27 (10).

7-Isopropyl-2,3,3-trimethyl-2H-benzofuran

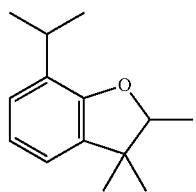

$^1$H-NMR (400 MHz, $CDCl_3$): δ = 1.09 (s, 3H), 1.24 (dd, J = 7.0 Hz, J = 0.7 Hz, 6H), 1.30 (s, 3H), 1.36 (d, J = 6.6 Hz, 3H), 3.11 (hept., J = 6.7 Hz, 1H), 4.34 (q, J = 6.6 Hz, 1H), 6.83 (dd, J = 7.6 Hz, J = 7.3 Hz, 1H), 6.92 (dd, J = 7.3 Hz, J = 1.5 Hz, 1H), 7.01 (ddd, J = 7.6 Hz, J = 1.5 Hz, J = 0.6 Hz, 1H) ppm.
$^{13}$C-NMR (100 MHz, $CDCl_3$): δ = 14.58 (q), 22.44 (q), 22.48 (q), 23.21 (q), 26.17 (q), 27.89 (d), 43.72 (s), 88.33 (d), 119.72 (d), 120.47 (d), 124.51 (d), 130.61 (s), 137.08 (s), 155.65 (s) ppm.
MS (EI): m/z (%) = 204 (27), 189 (53), 147 (100), 133 (22), 119 (29), 115 (14), 91 (27), 77 (12), 43 (24), 41 (22)

7-tert.-Butyl-2,2,3-trimethyl-3H-benzofuran

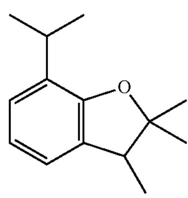

$^1$H-NMR (400 MHz, $CDCl_3$): δ = 1.19-1.26 (m, 12H), 1.47 (d, J = 0.5 Hz, 3H), 3.04 (hept., J = 6.9 Hz, 1H), 3.13 (dq, J = 7.3 Hz, J = 0.9 Hz, 1H), 6.80 (dd, J = 7.6 Hz, J = 7.3 Hz, 1H), 6.91-6.94 (m, 1H), 6.97-7.01 (m, 1H) ppm.
$^{13}$C-NMR (100 MHz, $CDCl_3$): δ = 14.61 (q), 21.94 (q), 22.17 (q), 22.31 (q), 28.04 (q), 28.09 (d), 45.82 (d), 88.86 (s), 119.94 (d), 121.20 (d), 124.61 (d), 130.48 (s), 132.36 (s), 155.59 (s) ppm.

-continued

| | |
|---|---|
| 1-(7-Isopropyl-2,3,3-trimethyl-2H-benzofuran-5-yl)ethanone 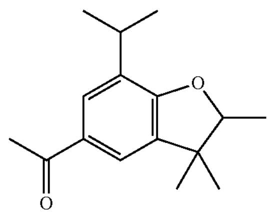 [SMILES: CC(=O)c1cc(C(C)C)c2c(c1)C(C)(C)C(C)O2] | $^1$H-NMR (400 MHz, $CDCl_3$): δ =1.12 (s, 3H), 1.27 (dd, J = 6.9 Hz, J = 0.9 Hz, 6H), 1.33 (s, 3H), 1.38 (d, J = 6.5 Hz, 3H), 2.56 (s, 3H), 3.12 (hept., J = 6.9 Hz, 1H), 4.46 (q, J = 6.6 Hz, 1H), 7.59 (d, J = 1.9 Hz, 1H), 7.70 (dd, J = 1.9 Hz, J = 0.6 Hz, 1H) ppm. $^{13}$C-NMR (100 MHz, $CDCl_3$): δ = 14.70 (q), 22.20 (q), 22.22 (q), 23.23 (q), 26.42 (q, q), 28.09 (d), 43.45 (s), 89.79 (d), 120.79 (d), 126.90 (d), 130.37 (s), 130.94 (s), 137.67 (s), 160.33 (s), 197.04 (s) ppm. MS (EI): m/z (%) = 246 (20), 232 (8), 231 (46), 189 (11), 175 (7), 147 (10), 115 (7), 91 (8), 43 (100), 41 (9). |
| 1-Methyl-4-(3-methylbut-2-enoxy)benzene 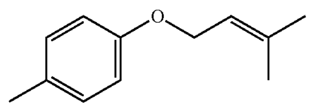 | $^1$H-NMR (400 MHz, $CDCl_3$): δ = 1.70-1.76 (m, 3H), 1.76-1.82 (m, 3H), 2.25-2.32 (m, 3H), 4.42-4.53 (m, 2H), 5.44-5.55 (m, 1H), 6.75-6.86 (m, 2H), 7.01-7.12 (m, 2H) ppm. $^{13}$C-NMR (100 MHz, $CDCl_3$): δ = 18.17 (q), 20.46 (q), 25.83 (q), 64.78 (t), 114.49 (d, d), 119.91 (d), 129.77 (s), 129.83 (d, d), 137.93 (s), 156.72 (s) ppm. MS (EI): m/z (%) = 109 (8), 108 (100), 107 (23), 79 (9), 77 (14), 69 (20), 53 (10), 41 (35), 39 (13), 27 (9). |
| 2,3,3,5-Tetramethyl-2H-benzofuran 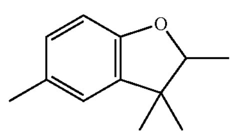 | $^1$H-NMR (400 MHz, $CDCl_3$): δ = 1.08 (s, 3H), 1.29 (s, 3H), 1.36 (d, J = 6.5 Hz, 3H), 2.29 (s, 3H), 4.34 (q, J = 6.6 Hz, 1H), 6.63-6.68 (m, 1H), 6.86-6.93 (m, 2H) ppm. $^{13}$C-NMR (100 MHz, $CDCl_3$): δ = 14.40 (q), 20.90 (q), 23.23 (q), 25.86 (q), 43.66 (s), 88.83 (d), 109.08 (d), 123.07 (d), 128.09 (d), 129.78 (s), 137.59 (s) 156.06 (s) ppm. MS (EI): m/z (%) = 176 (46), 162 (12), 161 (100), 133 (48), 115 (16), 105 (36), 91 (18), 77 (11), 41 (11), 39 (10). |
| 2,3,3,5-Tetramethyl-2H-benzofuran-7-carbaldehyde 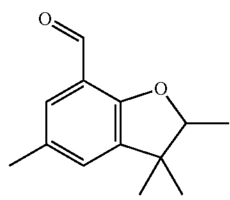 | $^1$H-NMR (400 MHz, $CDCl_3$): δ = 1.12 (s, 3H), 1.32 (s, 3H), 1.42 (d, J = 6.6 Hz, 3H), 2.31-2.33 (m, 3H), 4.51 (q, J = 6.6 Hz, 1H), 7.09-7.11 (m, 1H), 7.35-7.39 (m, 1H), 10.19-10.20 (m, 1H). ppm. $^{13}$C-NMR (100 MHz, $CDCl_3$): δ = 14.59 (q), 20.67 (q), 23.27 (q), 26.13 (q), 43.01 (s), 90.75 (d), 119.16 (s), 126.46 (d), 129.68 (d), 130.21 (s), 140.00 (s), 158.92 (s), 188.95 (d). ppm |
| 1-(2,3,3,5-Tetramethyl-2H-benzofuran-7-yl)ethanone 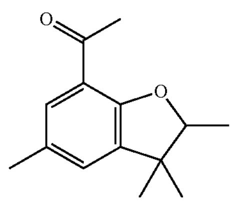 | $^1$H-NMR (400 MHz, $CDCl_3$): δ = 1.23 (d, J = 1.1 Hz, 3H), 1.31 (s, 3H), 1.51 (s, 3H), 2.29 (s, 3H), 2.60 (s, 3H), 4.47 (q, J = 6.6 Hz, 1H), 7.04-7.08 (m, 1H), 7.41-7.54 (m, 1H) ppm. $^{13}$C-NMR (100 MHz, $CDCl_3$): δ = 14.69 (q), 20.59 (q), 22.09 (q), 28.08 (q), 31.23 (q), 45.04 (s), 91.05 (d), 120.21 (s), 127.54 (d), 129.31 (s), 129.75 (d), 135.33 (s), 156.81 (s), 197.55 (s) ppm. |
| 2,2,3,5-Tetramethyl-3H-benzofuran 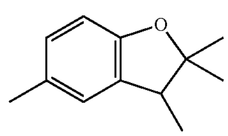 | $^1$H-NMR (400 MHz, $CDCl_3$): δ = 1.21 (d, J = 7.1 Hz, 3H), 1.26-1.27 (m, 3H), 1.44-1.47 (m, 3H), 2.28 (s, 3H), 3.11 (q, J = 7.1 Hz, 1H), 6.61 (d, J = 8.5 Hz, 1H), 6.88-6.92 (m, 2H) ppm. |
| 1-Methyl-2-(3-methylbut-2-enoxy (benzene 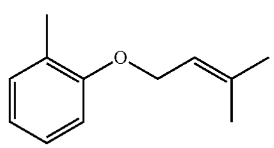 | $^1$H-NMR (400 MHz, $CDCl_3$): δ = 1.73 (s, 3H), 1.79 (s, 3H), 2.23 (s, 3H), 4.52 (d, J = 6.5 Hz, 2H), 5.58-5.43 (m, 1H), 6.89-6.78 (m, 2H), 7.18-7.07 (m, 2H) ppm. $^{13}$C-NMR (100 MHz, $CDCl_3$): δ = 16.32 (q), 18.23 (q), 25.79 (q), 65.00 (t), 111.36 (d), 120.20 (d), 120.33 (d), 126.63 (d), 127.02 (s), 130.62 (d), 137.08 (s), 157.05 (s) ppm. MS (EI): m/z (%) = 109 (8), 108 (100), 107 (14), 80 (4), 79 (5), 77 (8), 69 (26), 41 (27), 39 (6), 27 (4). |

-continued

| | |
|---|---|
| 2,3,3,7-Tetramethyl-2H-benzofuran 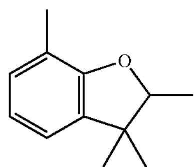 | $^1$H-NMR (400 MHz, $CDCl_3$): δ = 1.08 (s, 3H), 1.30 (s, 3H), 1.38 (d, J = 6.6 Hz, 3H), 2.22 (s, 3H), 4.35 (q, J = 6.6 Hz, 1H), 6.78 (dd, J = 7.4 Hz, 1H), 6.89-6.95 (m, 2H) ppm. $^{13}$C-NMR (100 MHz, $CDCl_3$): δ = 14.48 (q), 15.15 (q), 23.27 (q), 26.03 (q), 43.81 (s), 88.46 (d), 119.62 (s), 119.76 (d), 120.37 (d), 129.02 (d), 136.88 (s), 156.58 (s) ppm. MS (EI): m/z (%) = 176 (49), 161 (100), 133 (45), 117 (14), 115 (18), 105 (30), 91 (28), 77 (17), 41 (14), 39 (17). |
| 1-(2,2,3,7-Tetramethyl-3H-benzofuran-5-yl)ethanone 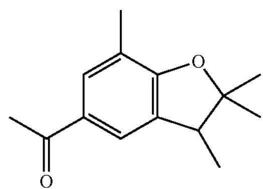 [SMILES: CC(=O)c1cc(C)c2c(c1)C(C)C(C)(C)O2] | $^1$H-NMR (400 MHz, $CDCl_3$): δ = 1.25 (d, J = 7.2 Hz, 3H), 1.29 (s, 3H), 1.50 (s, 3H), 2.22 (s, 3H), 2.53 (s, 3H), 3.17 (q, J = 7.0 Hz, 1H), 7.59-7.60 (m, 1H), 7.61-7.63 (m, 1H) ppm. $^{13}$C-NMR (100 MHz, $CDCl_3$): δ = 14.74 (q), 15.18 (q), 22.09 (q), 26.43 (q), 28.15 (q), 45.47 (d), 91.08 (s), 119.29 (s), 122.30 (d), 130.29 (s), 131.39 (d), 132.69 (s), 161.07 (s), 197.00 (s) ppm. MS (EI): m/z (%) = 219 (7), 218 (43), 204 (14), 203 (100), 161 (15), 147 (12), 115 (11), 91 (11), 43 (66), 41 (7). |
| 1-Methyl-3-(3-methylbut-2-enoxy)benzene 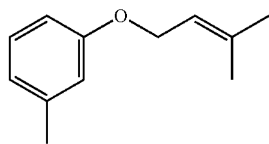 | $^1$H-NMR (400 MHz, $CDCl_3$): δ = 1.74 (s, 3H), 1.79 (s, 3H), 2.32 (s, 3H), 4.49 (d, J = 6.8 Hz, 2H), 5.42-5.54 (m, 1H), 6.67-6.80 (m, 3H), 7.15 (ddd, J = 8.0 Hz, J = 7.2 Hz, J = 0.9 Hz, 1H) ppm. $^{13}$C-NMR (100 MHz, $CDCl_3$): δ = 18.17 (q), 21.55 (q), 25.83 (q), 64.58 (t), 111.50 (d), 115.48 (d), 119.83 (d), 121.40 (d), 129.12 (d), 137.97 (s), 139.40 (s), 158.87 (s) ppm. MS (EI): m/z (%) = 109 (8), 108 (100), 107 (18), 79 (8), 77 (12), 69 (24), 53 (8), 41 (36), 39 (12), 27 (7). |
| 2,3,3,6-tetramethyl-2H-benzofuran 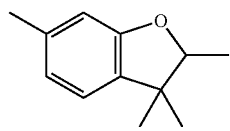 | $^1$H-NMR (400 MHz, $CDCl_3$): δ = 1.08 (s, 3H), 1.29 (s, 3H), 1.35 (d, J = 6.6 Hz, 3H), 2.30 (s, 3H), 4.35 (q, J = 6.6 Hz, 1H), 6.59 (dd, J = 1.4 Hz, J = 0.7 Hz, 1H), 6.69 (ddd, J = 7.5 Hz, J = 1.5 Hz, J = 0.7 Hz, 1H), 6.96 (dd, J = 7.4 Hz, J = 0.4 Hz, 1H) ppm. $^{13}$C-NMR (100 MHz, $CDCl_3$): δ = 14.48 (q), 21.49 (q), 23.30 (q), 26.11 (q), 43.38 (s), 88.99 (d), 110.30 (d), 121.19 (d), 122.06 (d), 134.73 (s), 137.89 (s), 158.42 (s) ppm. |
| 1-(2,3,3,4-Tetramethyl-2H-benzofuran-5-yl)ethanone 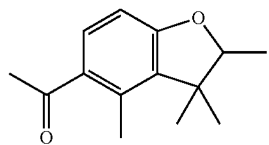 [SMILES: CC(=O)c1ccc2c(c1C)C(C)(C)C(C)O2] | $^1$H-NMR (400 MHz, $CDCl_3$): δ = 1.16 (s, 3H), 1.37 (d, J = 6.5 Hz, 3H), 1.42 (s, 3H), 2.53 (s, 3H), 2.53 (s, 3H), 4.30 (q, J = 6.5 Hz, 1H), 6.63 (dd, J = 8.4 Hz, J = 0.5 Hz, 1H), 7.56 (dd, J = 8.4 Hz, J = 0.4 Hz, 1H) ppm. $^{13}$C-NMR (100 MHz, $CDCl_3$): δ = 13.67 (q), 16.27 (q), 20.86 (q), 25.25 (q), 29.73 (q), 44.55 (s), 88.82 (d), 106.81 (d), 131.30 (d), 132.12 (s), 136.01 (s), 136.68 (s), 161.18 (s), 200.72 (s) ppm |
| 1-(2,3,3,4-Tetramethyl-2H-benzofuran-7-yl)ethanone 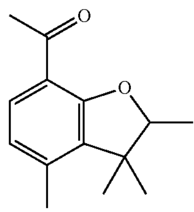 [SMILES: CC(=O)c1ccc(C)c2c1OC(C)C2(C)C] | $^1$H-NMR (400 MHz, $CDCl_3$): δ = 1.16 (s, 3H), 1.38-1.44 (m, 6H), 2.39 (s, 3H), 2.60 (s, 3H), 4.38 (q, J = 6.5 Hz, 1H), 6.66 (dd, J = 8.1 Hz, J = 0.6 Hz, 1H), 7.59 (dd, J = 8.1 Hz, J = 0.4 Hz, 1H) ppm. $^{13}$C-NMR (100 MHz, $CDCl_3$): δ = 13.94 (q), 18.46 (q), 20.79 (q), 25.07 (q), 31.05 (q), 43.81 (s), 88.82 (d), 119.20 (s), 123.51 (d), 127.91 (d), 135.77 (s), 140.11 (s), 159.14 (s), 197.11 (s) ppm. |
| 1-(2,3,3,6-Tetramethyl-2H-benzofuran-5-yl)ethanone 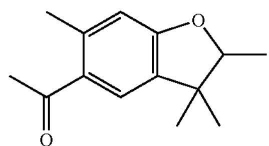 [SMILES: CC(=O)c1cc2c(cc1C)OC(C)C2(C)C] | $^1$H-NMR (400 MHz, $CDCl_3$): δ = 1.12 (s, 3H), 1.34 (s, 3H), 1.38 (d, J = 6.6 Hz, 3H), 2.53 (s, 3H), 2.56 (s, 3H), 4.45 (q, J = 6.6 Hz, 1H), 6.58-6.65 (m, 1H), 7.48 (s, 1H) ppm. $^{13}$C-NMR (100 MHz, $CDCl_3$): δ = 14.59 (q), 22.76 (q), 23.35 (q), 26.33 (q), 29.37 (q), 43.30 (s), 90.05 (d), 113.03 (d), 124.86 (d), 130.47 (s), 134.99 (s), 141.40 (s), 161.13 (s), 199.53 (s) ppm. |

-continued

1-Isopropyl-4-methyl-2-(3-methylbut-2-enoxy)benzene

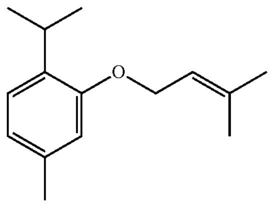 [SMILES: CC(C)=CCOc1cc(C)ccc1C(C)C]

$^1$H-NMR (400 MHz, $CDCl_3$): δ = 1.19 (d, J = 6.9 Hz, 6H), 1.73 (s, 3H), 1.78 (s, 3H), 2.31 (s, 3H), 3.30 (hept., J = 6.9 Hz, 1H), 4.50 (dt, J = 6.6 Hz, J = 1.0 Hz, 2H), 5.43-5.55 (m, 1H), 6.65-6.68 (m, 1H), 6.73 (dd, J = 7.7 Hz, J = 1.8 Hz, 1H), 7.08 (d, J = 7.7 Hz, 1H) ppm.
$^{13}$C-NMR (100 MHz, $CDCl_3$): δ = 18.22 (q), 21.36 (q), 22.84 (q, q), 25.77 (q), 26.47 (d), 65.08 (t), 112.74 (d), 120.46 (d), 121.06 (d), 125.82 (d), 134.38 (s), 136.11 (s), 136.89 (s), 155.98 (s) ppm.
MS (EI): m/z (%) = 150 (42), 136 (11), 135 (100), 115 (6), 91 (13), 77 (6), 69 (30), 41 (35), 39 (8), 27 (5).

7-Isopropyl-2,3,3,4-tetramethyl-2H-benzofuran

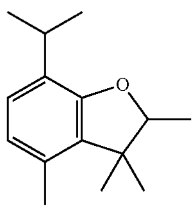 [SMILES: Cc1ccc(C(C)C)c2c1C(C)(C)C(C)O2]

$^1$H-NMR (400 MHz, $CDCl_3$): δ = 1.12 (s, 3H), 1.22 (dd, J = 6.9 Hz, 6H), 1.36 (d, J = 6.5 Hz, 3H), 1.38 (s, 3H), 2.33 (s, 3H), 3.09 (hept., J = 6.3 Hz, 1H), 4.25 (q, J = 6.5 Hz, 1H), 6.60 (d, J = 7.7 Hz, 1H), 6.91 (d, J = 7.7 Hz, 1H) ppm.
$^{13}$C-NMR (100 MHz, $CDCl_3$): δ = 13.88 (q), 17.94 (q), 20.86 (q), 22.51 (q), 22.62 (q), 25.10 (q), 27.48 (d), 44.61 (s), 87.49 (d), 122.94 (d), 124.37 (d), 128.40 (s), 131.46 (s), 133.64 (s), 155.92 (s) ppm.
MS (EI): m/z (%) = 218 (46), 203 (93), 161 (100), 147 (26), 133(26), 115 (15), 105 (16), 91 (16), 43 (23), 41 (22).

1-(7-Isopropyl-2,3,3,4-tetramethyl-2H-benzofuran-5-yl)ethanone

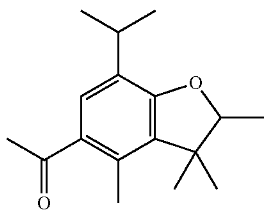 [SMILES: CC(=O)c1cc(C(C)C)c2c(c1C)C(C)(C)C(C)O2]

$^1$H-NMR (400 MHz, $CDCl_3$): δ = 1.15 (s, 3H), 1.24 (d, J = 6.9 Hz, 6H), 1.37 (d, J = 6.5 Hz, 3H), 1.41 (s, 3H), 2.49 (s, 3H), 2.54 (s, 3H), 3.09 (hept., J = 6.7 Hz, 1H), 4.28 (q, J = 6.5 Hz, 1H), 7.42 (s, 1H) ppm.
$^{13}$C-NMR (100 MHz, $CDCl_3$): δ = 13.80 (q), 15.97 (q), 20.87 (q), 22.25 (q), 22.34 (q), 25.36 (q), 27.69 (d), 29.84 (q), 44.66 (s), 88.41 (d), 127.50 (s), 127.80 (d), 132.15 (s), 133.57 (s), 135.50 (s), 158.83 (s), 201.18 (s) ppm.
MS (EI): m/z (%) = 260 (36), 246 (18), 245 (100), 203 (13), 161 (16), 128 (7), 115 (10), 91 (7), 43 (91), 41 (10).

7-Isopropyl-2,3,3,4-tetramethyl-2H-benzofuran-5-carbaldehyde oxime

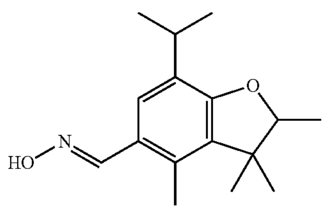 [SMILES: Cc1c(/C=N/O)cc(C(C)C)c2c1C(C)(C)C(C)O2]

$^1$H-NMR (400 MHz, $CDCl_3$): δ = 1.14 (s, 3H), 1.20-1.24 (m, 6H), 1.37 (d, J = 6.5 Hz, 3H), 1.40 (s, 3H), 2.38 (s, 3H), 3.08 (hept., J = 6.9 Hz, 1H), 4.27 (q, J = 6.5 Hz, 1H), 7.36-7.40 (m, 1H), 8.24 (s, 1H), 8.38-8.42 (m, 1H) ppm.
$^{13}$C-NMR (100 MHz, $CDCl_3$): δ = 13.81 (q), 14.20 (q), 21.12 (q), 22.31 (q), 22.41 (q), 25.49 (q), 27.61 (d), 44.67 (s), 88.07 (d), 123.50 (s), 124.25 (d), 128.95 (s), 131.11 (s), 134.49 (s), 149.66 (d), 157.75 (s) ppm.
MS (EI): m/z (%) = 261 (90), 246 (100), 244 (28), 243 (30), 228 (78), 204 (49), 187 (33), 186 (90), 43 (30), 41 (23).

7-Isopropyl-2,3,3,4-tetramethyl-2H-benzofuran-5-carbonitrile

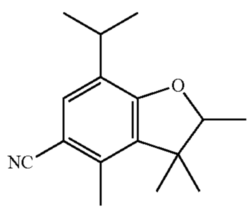 [SMILES: Cc1c(C#N)cc(C(C)C)c2c1C(C)(C)C(C)O2]

$^1$H-NMR (400 MHz, $CDCl_3$): δ = 1.14 (s, 3H), 1.20 (d, J = 6.9 Hz, 6H), 1.37 (d, J = 6.5 Hz, 3H), 1.39 (s, 3H), 2.50 (s, 3H), 3.06 (hept., J = 6.9 Hz, 1H), 4.33 (q, J = 6.6 Hz, 1H), 7.27-7.29 (m, 1H) ppm.
$^{13}$C-NMR (100 MHz, $CDCl_3$): δ = 13.85 (q), 16.01 (q), 20.93 (q), 22.05 (q), 22.12 (q), 25.15 (q), 27.44 (d), 44.66 (s), 88.65 (d), 105.26 (s), 119.55 (s), 129.68 (s), 130.37 (d), 134.83 (s), 135.78 (s), 159.64 (s) ppm.
MS (EI): m/z (%) = 244 (6), 243 (33), 229 (11), 228 (67), 187 (14), 186 (100), 172 (19), 115 (5), 106 (5), 43 (5).

3-Methylbut-2-enoxybenzene

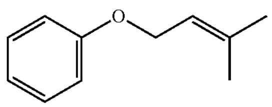

$^1$H-NMR (200 MHz, $CDCl_3$): δ = 1.75 (s, 3H), 1.80 (s, 3H), 4.51 (d, J = 6.8 Hz, 2H), 5.40-5.60 (m, 1H), 6.85-7.01 (m, 3H), 7.14-7.39 (m, 2H) ppm.
$^{13}$C-NMR (50 MHz, $CDCl_3$): δ = 18.12 (q), 25.78 (q), 64.50 (t), 114.48 (d, d), 119.67 (d), 120.43 (d), 129.25 (d, d), 137.81 (s), 158.65 (s) ppm.
MS (EI): m/z (%) = 162 (7), 95 (7), 94 (100), 69 (32), 67 (8), 66 (5), 65 (8), 53 (5), 41 (33), 39 (12).

-continued

| | |
|---|---|
| 2,3,3-Trimethyl-2H-benzofuran 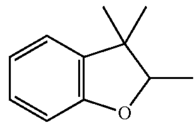 | $^{1}$H-NMR (400 MHz, $CDCl_3$): δ = 1.09 (s, 3H), 1.31 (s, 3H), 1.37 (d, J = 6.6 Hz, 3H), 4.37 (q, J = 6.5 Hz, 1H), 6.74-6.79 (m, 1H), 6.83-6.90 (m, 1H), 7.04-7.14 (m, 2H) ppm. $^{13}$C-NMR (100 MHz, $CDCl_3$): δ = 14.43 (q), 23.26 (q), 25.96 (q), 43.61 (s), 88.76 (d), 109.53 (d), 120.53 (d), 122.46 (d), 127.76 (d), 137.57 (s), 158.18 (s) ppm. MS (EI): m/z (%) = 162 (50), 148 (12), 147 (100), 131 (8), 119 (41), 103 (8), 91 (34), 77 (10), 41 (7), 39 (7). |
| 1-(2,3,3,4,7-Pentamethyl-2H-benzofuran-5-yl)ethanone 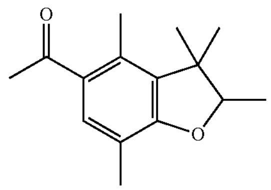 [SMILES: CC(=O)c1cc(C)c2c(c1C)C(C)(C)C(C)O2] | $^{1}$H-NMR (400 MHz, $CDCl_3$): δ = 1.15 (s, 3H), 1.38 (d, J = 6.5 Hz, 3H), 1.41 (s, 3H), 2.20 (s, 3H), 2.49 (s, 3H), 2.53 (s, 3H), 4.28 (q, J = 6.5 Hz, 1H), 7.36-7.38 (m, 1H) ppm. $^{13}$C-NMR (100 MHz, $CDCl_3$): δ = 13.72 (q), 14.96 (q), 15.95 (q), 20.85 (q), 25.31 (q), 29.81 (q), 44.79 (s), 88.52 (d), 116.57 (s), 131.90 (s), 132.23 (d), 133.79 (s), 135.27 (s), 159.67 (s), 200.96 (s) ppm |
| 2,3,3,4,7-Pentamethyl-2H-benzofuran-5-carbaldehyde 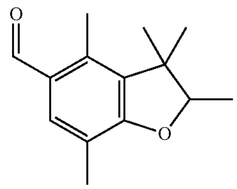 [SMILES: Cc1cc(C=O)c(C)c2c1OC(C)C2(C)C] | $^{1}$H-NMR (400 MHz, $CDCl_3$): δ = 1.17 (s, 3H), 1.40 (d, J = 6.6 Hz, 3H), 1.43 (s, 3H), 2.21 (s, 3H), 2.64 (s, 3H), 4.35 (q, J = 6.6 Hz, 1H), 7.44-7.45 (m, 1H), 10.06 (s, 1H) ppm. $^{13}$C-NMR (100 MHz, $CDCl_3$): δ = 13.78 (q), 13.82 (q), 14.73 (q), 21.11 (q), 25.47 (q), 44.45 (s), 89.01 (d), 117.93 (s), 128.58 (s), 135.16 (s), 135.81 (s), 135.96 (d), 161.90 (s), 191.57 (d) ppm. |
| 2,3,3,4,6,7-Hexamethyl-2H-benzofuran-5-carbaldehyde 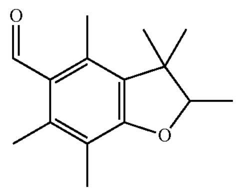 | $^{1}$H-NMR (400 MHz, $CDCl_3$): δ = 1.15 (s, 3H), 1.38 (d, J = 6.5 Hz, 3H), 1.41 (s, 3H), 2.14 (s, 3H), 2.47 (s, 3H), 2.56 (s, 3H), 4.28 (q, J = 6.5 Hz, 1H), 10.51 (s, 1H) ppm. $^{13}$C-NMR (100 MHz, $CDCl_3$): δ = 11.54 (q), 13.76 (q), 15.12 (q), 15.46 (q), 21.14 (q), 25.62 (q), 44.70 (s), 88.38 (d), 117.46 (s), 127.48 (s), 132.36 (s), 135.74 (s), 141.84 (s), 160.93 (s), 193.16 (d) ppm |
| 1-(2,3,3,4,6,7-Hexamethyl-2H-benzofuran-5-yl)ethanone 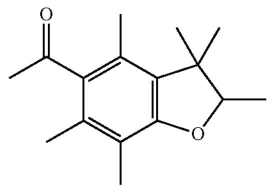 [SMILES: CC(=O)c1c(C)c(C)c2c(c1C)C(C)(C)C(C)O2] | $^{1}$H-NMR (400 MHz, $CDCl_3$): δ = 1.10 (s, 3H), 1.36 (d, J = 6.4 Hz, 3H), 1.37 (s, 3H), 2.09 (s, 6H), 2.20 (s, 3H), 2.45 (s, 3H), 4.23 (q, J = 6.5 Hz, 1H) ppm. $^{13}$C-NMR (100 MHz, $CDCl_3$): δ = 11.45 (q), 13.73 (q), 14.79 (q), 16.15 (q), 20.90 (q), 25.25 (q), 33.23 (q), 45.00 (s), 87.81 (d), 116.68 (s), 125.67 (s), 130.96 (s), 131.60 (s), 136.62 (s), 157.06 (s), 209.88 (s). ppm. |
| 1-(6-Isopropyl-2,3,3,4-tetramethyl-2H-benzofuran-5-yl)ethanone 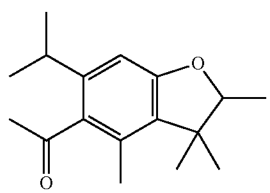 [SMILES: CC(=O)c1c(C(C)C)cc2c(c1C)C(C)(C)C(C)O2] | $^{1}$H-NMR (400 MHz, $CDCl_3$): δ = 6.58 (s, 1H), 4.26 (q, J = 6.5 Hz, 1H), 2.71 (hept, J = 6.8 Hz, 1H), 2.47 (s, 3H), 2.22 (d, J = 0.4 Hz, 3H), 1.38 (s, 3H), 1.35 (d, J = 6.5 Hz, 3H), 1.20 (d, J = 6.8 Hz, 3H), 1.19 (d, J = 6.8 Hz, 3H), 1.12 (s, 3H) ppm. $^{13}$C-NMR (100 MHz, $CDCl_3$): δ = 209.68 (s), 159.03 (s), 144.48 (s), 135.52 (s), 132.54 (s), 128.70 (s), 104.60 (d), 88.37 (d), 44.63 (s), 33.79 (q), 31.05 (d), 25.24 (q), 24.42 (q), 24.25 (q), 21.05 (q), 15.10 (q), 13.80 (q) ppm |

-continued

| | |
|---|---|
| 1-(6-Isopropyl-2,3,3,4-tetramethyl-2H-benzofuran-7-yl)ethanone 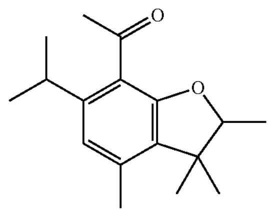 [SMILES: CC(=O)c1c(C(C)C)cc(C)c2c1OC(C)C2(C)C] | $^1$H-NMR (400 MHz, $CDCl_3$): δ = 6.59 (s, 1H), 4.31 (q, J = 6.5 Hz, 1H), 3.16 (hept, J = 6.9 Hz, 1H), 2.55 (s, 3H), 2.34 (d, J = 0.6 Hz, 4H), 1.37 (s, 3H), 1.34 (d, J = 6.5 Hz, 3H), 1.19 (d, J = 6.8 Hz, 3H), 1.18 (d, J = 6.8 Hz, 3H), 1.12 (s, 3H) ppm. $^{13}$C-NMR (100 MHz, $CDCl_3$): δ = 203.40 (s), 156.30 (s), 146.47 (s), 136.20 (s), 132.01 (s), 121.39 (s), 120.61 (d), 88.67 (d), 43.89 (s), 32.54 (q), 29.13 (d), 25.12 (q), 24.36 (q), 24.24 (q), 20.86 (q), 18.39 (q), 13.91 (q) ppm. |

Example 6

Perfume Composition (Fragrance Mixture/Fragrance Composition)

| | |
|---|---|
| Agrumex LC | 10.00 |
| Amarocit ® 10% in DPG | 10.00 |
| Ambroxide cryst. | 10.00 |
| Basil oil | 10.00 |
| Calone 1951 10% in DPG | 10.00 |
| Cedarwood oil | 10.00 |
| Cedrol cryst | 50.00 |
| Citral 10% in DPG | 10.00 |
| Citonellol | 5.00 |
| Coumarin | 10.00 |
| Cyclogalbanat ® 10% in DPG | 15.00 |
| Dihydromyrcenol | 80.00 |
| Farenal ® 10% in DPG | 5.00 |
| Galbex 10% in DPG | 25.00 |
| Geraniol | 80.00 |
| Geranyl nitrile | 40.00 |
| Hedione | 90.00 |
| Helional | 20.00 |
| Heliotropin | 5.00 |
| Hexenol cis-3 10% in DPG | 15.00 |
| Hexenylsalicylate cis-3 | 10.00 |
| Beta-ionone | 5.00 |
| Iso E super | 180.00 |
| Isodamascon ® 10% in DPG | 10.00 |
| Isogalbanate | 20.00 |
| Isoraldein 70 | 20.00 |
| Ketamber 10% in TEC | 25.00 |
| Lavandin Oil Grosso Nat. | 15.00 |
| Lilial | 20.00 |
| Linalool | 20.00 |
| Linalyl acetate | 40.00 |
| Mandarin oil brasil. Green | 50.00 |
| Timberol ® | 40.00 |
| Vanillin | 5.00 |
| Veloutone 10% in DPG | 20.00 |
| Ysamber K ® | 10.00 |
| Total | 1000.00 |

DPG: dipropylene glycol, TEC = triethyl citrate

Odor description of the perfume composition without additive: fresh, woody.

In the opinion of the perfumers, for example by adding 3 wt % of 1-(7-isopropyl-2,3,3,4-tetramethyl-2H-benzofuran-5-yl)-ethanone (compound 2) this perfume composition becomes fresher, more radiant, more rounded and more harmonious, wherein a musky and sweet note is added and the woody and floral aspects are intensified. The compounds of formula (I) to be used according to the invention and corresponding mixtures thereof give a composition above (or some other), through its own odor and/or through its modifying and/or intensifying action (booster effect), advantageously a character of its own and link together the various olfactory elements.

Example 7

Perfume Composition (Fragrance Composition)

| | |
|---|---|
| Allylcyclohexyl propionate | 3.00 |
| Amyl salicylate | 2.00 |
| Benzyl acetate | 64.00 |
| Citronellol | 122.00 |
| Citral 10% in DPG | 2.00 |
| Cyclamen aldehyde | 10.00 |
| Dihydromyrcenol | 3.00 |
| Dimethylbenzylcarbinyl acetate | 3.00 |
| Ethyl salicylate 10% in DPG | 2.00 |
| Eugenol | 3.00 |
| Indoflor 10% in DPG | 16.00 |
| Galbaniff | 164.00 |
| Geraniol | 35.00 |
| Dihydromethyljasmonate | 6.00 |
| Heliotropin | 4.00 |
| Hexyl cinnamaldehyde | 121.00 |
| Vertocitral | 4.00 |
| Hydroxycitronellal | 42.00 |
| Indole | 2.00 |
| Isobutyl salicylate | 6.00 |
| Lavandin oil Grosso Nat. | 6.00 |
| Lactoscatone | 10.00 |
| Lilial | 190.00 |
| Linalool | 35.00 |
| Linalyl acetate | 10.00 |
| Methyl anthranilate 10% in DPG | 5.00 |
| Nerol | 10.00 |
| Orange oil | 6.00 |
| Paraxonal | 4.00 |
| Phenylacetaldehyde-dimethylacetal | 6.00 |
| Phenylethyl alcohol | 75.00 |
| Rosatol 10% in DPG | 6.00 |
| Sandalwood oil | 3.00 |
| Sandranol | 16.00 |
| TCD alcohol M | 2.00 |
| Trifernal | 2.00 |
| Total | 1000.00 |

DPG: dipropylene glycol

Odor description of the perfume composition without additive: floral, lily of the valley.

In the opinion of the perfumers, this perfume composition is revived in particular by adding 6 wt % of 1-(7-tert.-butyl-2,3,3-trimethyl-2H-benzofuran-5-yl)ethanone (compound 2). The floral impression is greatly intensified. The composition has a more radiant, more rounded and more harmonious effect, wherein a musky and natural note is added. The compounds of formula (I) to be used according to the invention and corresponding mixtures thereof endow the composition, through their own odor and through their modifying and intensifying action (booster effect), with a character of its own and link together the various olfactory elements.

Example 8

Shampoo

A mixture of 1-(7-tert.-butyl-2,3,3-trimethyl-2H-benzofuran-5-yl)ethanone (compound 2) and 7-isopropyl-2,3,3,4-tetramethyl-2H-benzofuran-5-carbonitrile was incorporated at a dosage of 0.5 wt % in a shampoo base with the following composition:

| | |
|---|---|
| Sodium lauryl ether sulfate (e.g. Texapon NSO, from Cognis Deutschland GmbH) | 12% |
| Cocamidopropylbetaine (e.g. Dehyton K, from Cognis Deutschland GmbH) | 2% |
| Sodium chloride | 1.4% |
| Citric acid | 1.3% |
| Phenoxyethanol, methyl-, ethyl-, butyl-, and propylparaben | 0.5% |
| Water | 82.8% |

The pH of the shampoo base was about 6. It was used for preparing 100 mL of a 20 wt % aqueous shampoo solution. In this shampoo solution, 2 locks of hair were washed together for 2 minutes and then rinsed for 20 seconds under running hand-warm water. One lock of hair was wrapped wet in aluminum foil and the second lock of hair was dried with a hair-dryer. Both locks of hair underwent olfactory assessment by a panel.

Odor description in each case: very strongly radiant, musky, exalting, softly woody, reminiscent of musk grains.

Example 9

Fabric Softener

The perfume composition from example 6 (after adding 6 wt % of compound of formula (I) as described) was incorporated in a dosage of 0.5 wt % in a fabric softener base with the following composition:

| | |
|---|---|
| Quaternary ammonium methosulfate (Esterquat), approx. 90%, (e.g. Rewoquat WE 18, from Witco Surfactants GmbH) | 5.5% |
| Alkyldimethylbenzylammonium chloride, approx. 50% (e.g. Preventol R50, from Bayer AG) | 0.2% |
| Coloring solution, approx. 1% | 0.3% |
| Water | 94.0% |

The pH of the fabric softener base was in the range from 2 through 3. Two pieces of cloth were rinsed with 370 g of a 1% aqueous fabric softener solution based on the fabric softener base comprising 0.5 wt % of compound of formula (I) in a Linetest machine in the soft-rinse programme for 30 minutes at 20° C. The cloths were wrung out and then spun for 20 seconds. One cloth was shrink-wrapped wet, and one was hung up to dry. Then both cloths underwent olfactory assessment by a panel.

Odor description in each case: floral, woody, fresh, radiant, musky and woody aspects with slight sweet undertones, rounded and harmonious odor impression.

Example 10

Washing Powder

The perfume oil composition from example 7 (after adding 6 wt % of compound of formula (I) as described) was incorporated in a dosage of 0.4 wt % in a washing powder base with the following recipe:

| | |
|---|---|
| Linear Na-alkylbenzene sulfonate | 8.8% |
| Ethoxylated fatty alcohol C12-18 (7 EO) | 4.7% |
| Na-soap | 3.2% |
| Antifoaming agent DOW CORNING ® 2-4248S POWDERED ANTIFOAM silicone oil on zeolite as carrier | 3.9% |
| Zeolite 4A | 28.3% |
| Na-carbonate | 11.6% |
| Na salt of a copolymer of acrylic and maleic acid (Sokalan CP5) | 2.4% |
| Na-silicate | 3.0% |
| Carboxymethylcellulose | 1.2% |
| Dequest 2066 ([[(Phosphonomethyl)imino]bis[(ethylenenitrilo)bis (methylene)]]tetrakis-phosphonic acid, sodium salt) | 2.8% |
| Optical brightener | 0.2% |
| Na-sulfate | 6.5% |
| Protease | 0.4% |
| Sodium perborate tetrahydrate | 22.0% |
| TAED | 1.0% |

Two pieces of cloth were washed with 370 g of a 1% aqueous washing powder lye based on the washing powder base comprising 0.4 wt % of the perfume oil composition from example 7 (the pH of the washing powder lye is definitely in the basic range) in a Linetest machine in the main wash cycle for 45 minutes at 60° C. The cloths were first rinsed with cold water for 5 minutes, wrung out and then spun for 20 seconds. One cloth was shrink-wrapped wet, and one was hung up to dry. Then both cloths underwent olfactory assessment by a panel.

Odor description in each case: strongly floral, radiant, musky and natural note with slight sweet and woody undertones, rounded and harmonious odor impression.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

We claim:

1. A method of imparting, modifying or intensifying an odour and/or taste, comprising incorporating a fragrance and/or flavoring material or fragrance and/or flavoring material mixture comprising, a compound of formula (I)

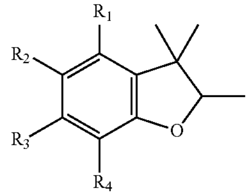

(I)

or a mixture of two or more different compounds of formula (I)

wherein $R_1$ and $R_4$, in each case independently of one another, denote methyl, ethyl, propyl, isopropyl, butyl, sec-butyl, tert-butyl, isobutyl, or cyano; $R_2$ denotes acetyl or formyl; and $R_3$ denotes hydrogen, methyl, ethyl, propyl, isopropyl, butyl, sec-butyl, tert-butyl, isobutyl or cyano.

2. The method of claim 1, wherein the fragrance and/or flavoring material or fragrance and/or flavoring material mixture produces a musky note.

3. The method of claim 1, wherein the method imparts, modifies and/or intensifies an odour and/or a taste selected from the group consisting of a musky odour, a radiant musky odour, an exalting odour, a woody odour and a softly woody odour, and combinations thereof.

4. The method of claim 1, wherein for a compound of formula (I), in each case independently from one another, $R_1$ denotes methyl, $R_2$ denotes formyl or acetyl, $R_3$ denotes hydrogen or methyl, and $R_4$ denotes methyl, ethyl, propyl, isopropyl, butyl, sec-butyl, tert-butyl or isobutyl.

5. The method of claim 1, wherein a compound of formula (I), in each case independently of one another, is selected from the group consisting of the following compounds 1 through 8:

COMPOUND 1

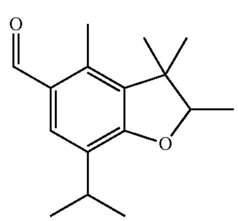

COMPOUND 2

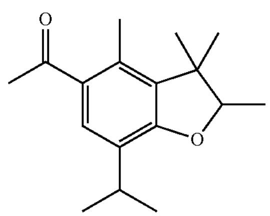

-continued

COMPOUND 3

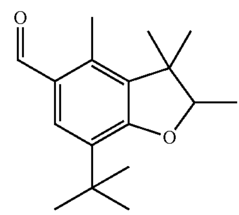

COMPOUND 4

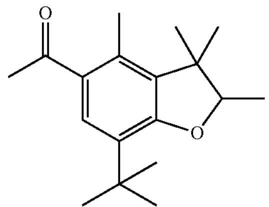

COMPOUND 5

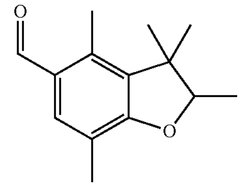

COMPOUND 6

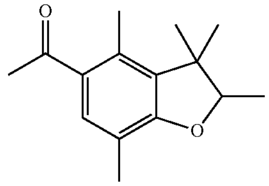

COMPOUND 7

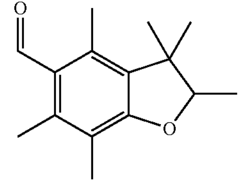

COMPOUND 8

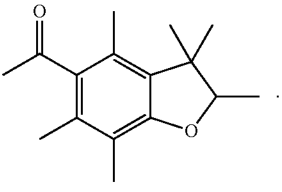

6. A fragrance and/or flavoring material mixture, comprising (a) a compound of formula (I)

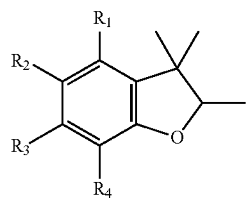

(I)

or a mixture of two or more different compounds of formula (I)

wherein $R_1$ and $R_4$, in each case independently of one another, denote methyl, ethyl, propyl, isopropyl, butyl, sec-butyl, tert-butyl, isobutyl, or cyano; $R_2$ denotes acetyl or formyl; $R_3$ denotes hydrogen, methyl, ethyl, propyl, isopropyl, butyl, sec-butyl, tert-butyl, isobutyl or cyano; and (b) one or more further fragrance and/or flavoring materials that are not compounds of formula (I).

7. The fragrance and/or flavoring material mixture of claim 6, wherein for a compound of formula (I), in each case independently from one another, $R_1$ denotes methyl, $R_2$ denotes formyl or acetyl, $R_3$ denotes hydrogen or methyl, and $R_4$ denotes methyl, ethyl, propyl, isopropyl, butyl, sec-butyl, tert-butyl or isobutyl.

8. The fragrance and/or flavoring material mixture as claimed in claim 6, wherein the one or more further fragrance or flavoring materials according to ingredient (b) impart a woody, a musky and/or a floral odour and/or taste.

9. The fragrance and/or flavoring material mixture of claim 6, wherein the total amount of compounds of formula (I) is in the range from 0.00001 through 99.9 wt % relative to the total weight of the fragrance or flavoring material mixture, and/or the weight ratio of the total amount of ingredient (a) to the total amount of ingredient (b) in the fragrance or flavoring material mixture is in the range from 1:100,000 through 10:1.

10. The fragrance and/or flavoring material mixture of claim 6, wherein the total amount of compounds of formula (I) is in the range from 0.001 through 70 wt %, relative to the total weight of the fragrance or flavoring material mixture.

11. The fragrance and/or flavoring material mixture of claim 6, wherein the total amount of compounds of formula (I) is in the range from 0.01 through 50 wt %, relative to the total weight of the fragrance or flavoring material mixture.

12. The fragrance and/or flavoring material mixture of claim 6, wherein the weight ratio of the total amount of ingredient (a) to the total amount of ingredient (b) in the fragrance or flavoring material mixture is in the range from 1:10,000 through 5:1.

13. The fragrance and/or flavoring material mixture of claim 6, wherein the weight ratio of the total amount of ingredient (a) to the total amount of ingredient (b) in the fragrance or flavoring material mixture is in the range from 1:1000 through 2:1.

14. A perfumed and/or flavored article comprising a fragrance and/or flavoring material mixture, wherein the fragrance and/or flavoring material mixture comprises (a) a compound of formula (I)

(I)

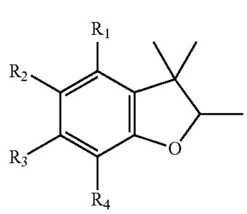

or a mixture of two or more different compounds of formula (I)

wherein $R_1$ and $R_4$, in each case independently of one another, denote methyl, ethyl, propyl, isopropyl, butyl, sec-butyl, tert-butyl, isobutyl, or cyano; $R_2$ denotes acetyl or formyl; $R_3$ denotes hydrogen, methyl, ethyl, propyl, isopropyl, butyl, sec-butyl, tert-butyl, isobutyl or cyano; and (b) one, two, three or a plurality of further fragrance and/or flavoring materials, wherein the further fragrance or flavoring material or materials are not compounds of formula (I).

15. The perfumed and/or flavored article of claim 14, wherein for a compound of formula (I), in each case independently from one another, $R_1$ denotes methyl, $R_2$ denotes formyl or acetyl, $R_3$ denotes hydrogen or methyl, and $R_4$ denotes methyl, ethyl, propyl, isopropyl, butyl, sec-butyl, tert-butyl or isobutyl.

16. The perfumed and/or flavored article as claimed in claim 14, wherein the article is selected from the group consisting of: perfume extracts, eaux de parfum, eaux de toilette, shaving lotions, eaux de Cologne, pre-shave products, splash Colognes, perfumed tissue wipes, acidic, alkaline and neutral cleaning agents, fabric fresheners, ironing aids, liquid detergents, powder detergents, washing pretreatment agents, fabric softeners, washing soaps, washing tablets, disinfectants, surface disinfectants, air fresheners, aerosol sprays, waxes and polishes, body-care products, hand creams and lotions, foot creams and lotions, depilatory creams and lotions, after-shave creams and lotions, tanning creams and lotions, hair care products, deodourants and antiperspirants, products of decorative cosmetics, candles, lamp oils, joss sticks, insecticides, repellents and propellants.

17. A compound of formula (I)

(I)

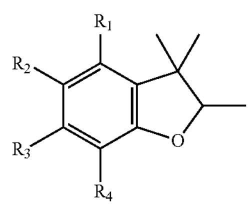

or a mixture of two or more different compounds of formula (I)

wherein for the residues of the compound of formula (I) or the residues of all compounds of formula (I), in each case independently of one another, $R_1$ denotes methyl, tert-butyl or cyano, $R_2$ denotes formyl or acetyl, $R_3$ denotes hydrogen, methyl or tert-butyl, and $R_4$ denotes methyl, ethyl, propyl, isopropyl, butyl, sec-butyl, tert-butyl, isobutyl or cyano.

18. The compound or mixture as claimed in claim 17, wherein for the residues of the compound of formula (I) or the residues of all compounds of formula (I), in each case independently of one another, $R_1$ denotes methyl, $R_2$ denotes formyl or acetyl, $R_3$ denotes hydrogen or methyl, and $R_4$ denotes methyl, ethyl, isopropyl or tert-butyl.

19. The compound or mixture as claimed in claim 17, wherein the compound of formula (I) or one, a plurality of or all compounds of formula (I) is selected, or in each case independently of one another, is/are selected, from the group consisting of the following compounds 1 through 8:

COMPOUND 1

COMPOUND 2

COMPOUND 3

COMPOUND 4

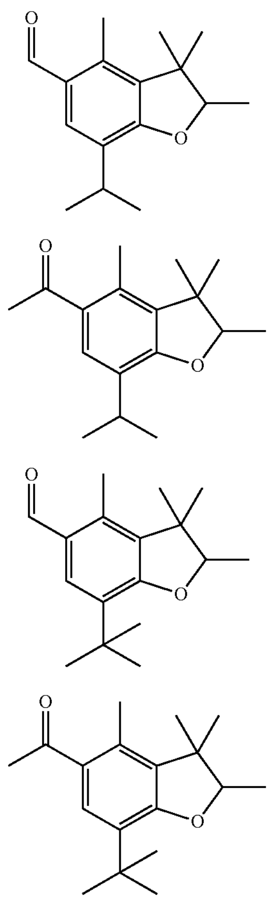

-continued

COMPOUND 5

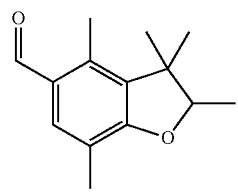

COMPOUND 6

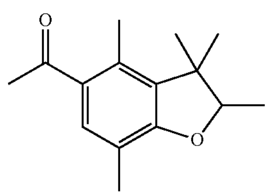

COMPOUND 7

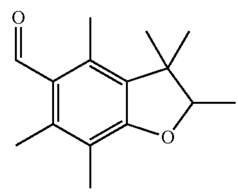

COMPOUND 8

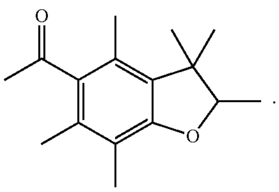

20. The compound or mixture as claimed in claim 19, wherein the compound of formula (I) or one, a plurality of or all compounds of formula (I) is selected, or in each case independently of one another, is/are selected, from the group consisting of the compounds 2, 4 and 5.

* * * * *